(12) United States Patent
King

(10) Patent No.: US 7,122,560 B2
(45) Date of Patent: Oct. 17, 2006

(54) LACTAM DERIVATIVES AS INHIBITORS OF MATRIX METALLOPROTEINASES AND/OR TNF-α CONVERTING ENZYME

(75) Inventor: Bryan W. King, Blue Bell, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 47 days.

(21) Appl. No.: 10/869,197

(22) Filed: Jun. 16, 2004

(65) Prior Publication Data

US 2004/0266751 A1   Dec. 30, 2004

Related U.S. Application Data

(60) Provisional application No. 60/479,308, filed on Jun. 18, 2003.

(51) Int. Cl.
*A61K 31/44* (2006.01)
*A61K 31/47* (2006.01)
*C07D 401/12* (2006.01)

(52) U.S. Cl. ............ 514/311; 514/13.4; 514/314; 566/187; 566/134; 566/172

(58) Field of Classification Search ........ 546/134, 546/187; 514/311, 317
See application file for complete search history.

(56) References Cited

U.S. PATENT DOCUMENTS 6,495,548 B1 * 12/2002 Duan ............... 514/231.5

6,825,215 B1 * 11/2004 Chen et al. ............... 514/314

FOREIGN PATENT DOCUMENTS

WO    WO 97/32846    9/1997

* cited by examiner

*Primary Examiner*—Rita Desai
(74) *Attorney, Agent, or Firm*—Jing G. Sun

(57) ABSTRACT

The present invention provides compounds of Formula (I):

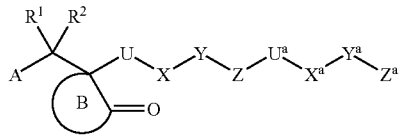

(I)

or a stereoisomer or pharmaceutically acceptable salt form thereof, wherein the variables A, B, $R^1$, $R^2$, U, X, Y, Z, $U^a$, $X^a$, $Y^a$, and $Z^a$ are defined are as defined herein, which are useful as inhibitors of matrix metalloproteinases (MMP), and/or TNF-α converting enzyme (TACE), or a combination thereof.

16 Claims, No Drawings

LACTAM DERIVATIVES AS INHIBITORS OF MATRIX METALLOPROTEINASES AND/OR TNF-α CONVERTING ENZYME

CROSS-REFERENCE TO RELATED APPLICATIONS

The present application claims the priority benefit of U.S. Provisional Application No. 60/479,308, filed Jun. 18, 2003, which is expressly incorporated fully herein by reference.

FIELD OF THE INVENTION

The present invention relates generally to novel lactam derivatives as inhibitors of matrix metalloproteinases (MMP), TNF-α converting enzyme (TACE), or a combination thereof, pharmaceutical compositions containing the same, and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitors of metalloprotease), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. *J. Bone Joint Surg.* 1970, 52A, 424–434). There are four classes of protein degradative enzymes in mammalian cells: serine, cysteine, aspartic and metalloproteases. The available evidence supports that it is the metalloproteases that are responsible for the degradation of the extracellular matrix of articular cartilage in OA and RA. Increased activities of collagenases and stromelysin have been found in OA cartilage and the activity correlates with severity of the lesion (Mankin et al. *Arthritis Rheum.* 1978, 21, 761–766, Woessner et al. *Arthritis Rheum.* 1983, 26, 63–68 and Woessner et al. *Arthritis Rheum.* 1984, 27, 305–312). In addition, aggrecanase has been identified as providing the specific cleavage product of proteoglycan found in RA and OA patients (Lohmander L. S. et al. *Arthritis Rheum.* 1993, 36, 1214–22).

Therefore, metalloproteases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. *Ann. Rep. Med. Chem.* 1990, 25, 175–184, AP, San Diego).

Tumor necrosis factor-α (TNF-α) is a cell-associated cytokine that is processed from a 26 kd precursor form to a 17 kd active form. TNF-α has been shown to be a primary mediator in humans and in animals, of inflammation, fever, and acute phase responses, similar to those observed during acute infection and shock. Excess TNF-α has been shown to be lethal. There is now considerable evidence that blocking the effects of TNF-α with specific antibodies can be beneficial in a variety of circumstances including autoimmune diseases such as rheumatoid arthritis (Feldman et al. *Lancet* 1994, 344, 1105), non-insulin dependent diabetes melitus (Lohmander, L. S. et al. *Arthritis Rheum.* 1993, 36, 1214–22) and Crohn's disease (MacDonald et al. *Clin. Exp. Immunol.* 1990, 81, 301).

Compounds which inhibit the production of TNF-α are therefore of therapeutic importance for the treatment of inflammatory disorders. Recently, TNF-α converting enzyme (TACE), the enzyme responsible for TNF-α release from cells, were purified and sequenced (Black et al. *Nature* 1997, 385, 729; Moss et al. *Nature* 1997, 385, 733). This invention describes molecules that inhibit this enzyme and hence the secretion of active TNF-α from cells. These novel molecules provide a means of mechanism based therapeutic intervention for diseases including but not restricted to septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV and non-insulin dependent diabetes melitus.

Since excessive TNF-α production has been noted in several disease conditions also characterized by MMP-mediated tissue degradation, compounds which inhibit both MMPs and TNF-α production may also have a particular advantage in diseases where both mechanisms are involved.

Prostaglandins (PG) play a major role in the inflammation process and the inhibition of PG production has been a common target of anti-inflammatory drug discovery. Many NSAIDS have been found to prevent the production of PG by inhibiting the enzyme cyclooxygenase (COX). Among the two isoforms of COXs, COX-1 is constitutively expressed. COX-2 is an inducible isozyme associated with inflammation. Selective COX-2 inhibitor was believed to maintain the efficacy of traditional NSAIDs, which inhibit both isozymes, and produce fewer and less drastic side effects. As a result, development of selective COX-2 inhibitors has attracted major interest in the pharmaceutical industry. Because of the significant roles of PGs and TNF-α in inflammation, combined use of COX-2 and TACE inhibitors may have superior efficacy to either therapy alone in some inflammatory diseases.

Human macrophage elastase (MMP-12) is expressed primarily by alveolar macrophages and is responsible for tissue remodelling by proteolytically degrading elastin. MMP-12 knockout mice appear to have a diminished capacity to degrade elastin, particularly in lung tissue, and appear less susceptible to pulmonary diseases such as emphysema (Hautamaki et al. *Science* 1997, 277, 2002–2004; Lanone et al. *J. Clin. Invest.* 2002, 110, 463–474). This invention describes molecules that inhibit the activity of MMP-12 and may circumvent undesired tissue destruction found in a variety of human diseases. These novel molecules provide a means of mechanism based therapeutic intervention for diseases including but not restricted to: emphysema, asthma, chronic obstructive pulmonary disease, cystic fibrosis, cancer, metastatic disease, atherosclerosis, and aneurysm.

WO97/32846 describes hydroxamic acid derivatives of the formula:

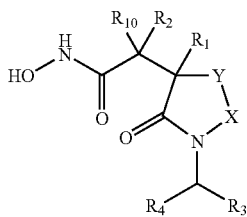

wherein X and Y can be carbon or nitrogen, $R_{1-4}$ and $R_{10}$ are a variety of substituents. Compounds specifically described in WO97/32846 are not considered to be part of the present invention.

It is desirable to find new compounds with improved pharmacological characteristics compared with known MMP and/or TACE inhibitors. For example, it is preferred to find new compounds with improved MMP and/or TACE inhibitory activity and selectivity for an MMP and/or TACE versus other metalloproteases (e.g., specificity for one MMP versus another). It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and, (g) factors that improve manufacturing costs or feasibility.

SUMMARY OF THE INVENTION

The compounds of the present invention act as inhibitors of MPs, in particular MMPs, and/or TACE, and/or aggrecanase. These novel molecules are provided as anti-inflammatory compounds and cartilage protecting therapeutics. The inhibition of TACE, aggrecanase, and other metalloproteases by molecules of the present invention indicates they are anti-inflammatory and should prevent the degradation of cartilage by these enzymes, thereby alleviating the pathological conditions of OA and RA.

The present invention provides novel lactam derivatives useful as MMP and/or TACE inhibitors or a stereoisomer or pharmaceutically acceptable salt, solvate, or prodrug thereof.

The present invention provides pharmaceutical compositions comprising a pharmaceutically acceptable carrier and a therapeutically effective amount of at least one of the compounds of the present invention or a stereoisomer or pharmaceutically acceptable salt, solvate, or prodrug thereof.

The present invention provides a method for treating inflammatory disorders, comprising: administering to a host, in need of such treatment, a therapeutically effective amount of at least one of the compounds of the present invention or a stereoisomer or pharmaceutically acceptable salt, solvate, or prodrug thereof.

The present invention provides a method of treating a condition or disease mediated by MMPs, TACE, or a combination thereof in a mammal, comprising: administering to the mammal in need of such treatment a therapeutically effective amount of a compound of the present invention or a stereoisomer or pharmaceutically acceptable salt, solvate, or prodrug thereof.

The present invention provides a method comprising: administering a compound of the present invention or a stereoisomer or pharmaceutically acceptable salt, solvate, or prodrug thereof, in an amount effective to treat a condition or disease mediated by MMPs, TACE, or a combination thereof.

The present invention provides a method for treating inflammatory disorders, comprising: administering, to a host in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

The present invention provides novel compounds of the present invention for use in therapy.

The present invention provides the use of novel compounds of the present invention for the manufacture of a medicament for the treatment of a condition or disease mediated by MMPs, TACE, or a combination thereof.

These and other features, which will become apparent during the following detailed description, have been achieved by the inventors' discovery that compounds of Formula (I):

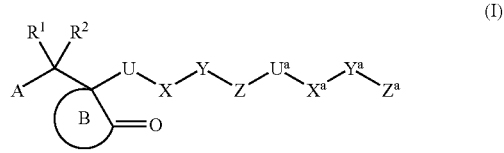

(I)

or a stereoisomer or pharmaceutically acceptable salt, solvate, or prodrug thereof, wherein A, B, $R^1$, $R^2$, U, X, Y, Z, $U^a$, $X^a$, $Y^a$, and $Z^a$ are defined below, are effective as MMP and/or TACE inhibitors.

DETAILED DESCRIPTION OF PREFERRED EMBODIMENTS

In a first aspect, the present invention provides, inter alia, compounds of Formula (I):

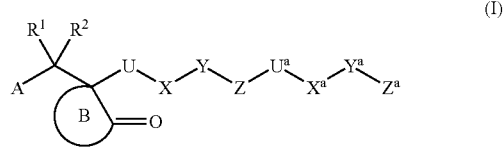

(I)

or a stereoisomer or pharmaceutically acceptable salt or solvate form thereof, wherein:

A is —C(O)NHOH, —C(O)NHOR$^5$, —C(O)NROR$^6$, —N(OH)COR$^5$, or —N(OH)CHO;

ring B is substituted with 0–3 R$^3$ and is a 4–9 membered ring consisting of carbon atoms, 0–3 heteroatoms selected from N, O, and S(O)$_p$, 0–1 additional carbonyl groups, and 0–3 double bonds;

U is absent or is O, NR$^{a1}$, C(O), CR$^a$(OH), C(O)O, OC(O), C(O)NR$^{a1}$, NR$^{a1}$C(O), OC(O)O, OC(O)NR$^{a1}$, NR$^{a1}$C(O)O, NR$^{a1}$C(O)NR$^{a1}$, S(O)$_p$, S(O)$_p$NR$^{a1}$, NR$^{a1}$S(O)$_p$, or NR$^{a1}$SO$_2$NR$^{a1}$;

X is absent or is C$_{1-10}$ alkylene, C$_{2-10}$ alkenylene, or C$_{2-10}$ alkynylene;

Y is absent or is O, NR$^{a1}$, S(O)$_p$, or C(O);

provided that U, X, and Y combine to form other than a NC(O) group;

Z is a C$_{3-13}$ carbocycle substituted with 0–5 R$^b$ or a 5–14 membered heterocycle consisting of carbon atoms and 1–4 heteroatoms selected from N, O, and S(O)$_p$, and substituted with 0–5 R$^b$;

U$^a$ is absent or is O, NR$^{a1}$, C(O), CR$^a$(OH), C(O)O, OC(O), C(O)NR$^{a1}$, NR$^{a1}$C(O), OC(O)O, OC(O)NR$^{a1}$, NR$^{a1}$C(O)O, NR$^{a1}$C(O)NR$^{a1}$, S(O)$_p$, S(O)$_p$NR$^{a1}$, NR$^{a1}$S(O)$_p$, or NR$^{a1}$SO$_2$NR$^{a1}$;

X$^a$ is absent or is C$_{1-10}$ alkylene, C$_{2-10}$ alkenylene, or C$_{2-10}$ alkynylene;

Y$^a$ is absent or is O, NR$^{a1}$, S(O)$_p$, or C(O);

Z$^a$ is C$_{3-13}$ carbocycle substituted with 0–5 R$^c$ or a 5–14 membered heterocycle consisting of carbon atoms and 1–4 heteroatoms selected from N, O, and S(O)$_p$, and substituted with 0–5 R$^c$;

provided that U, Y, Z, U$^a$, Y$^a$, and Z$^a$ do not combine to form a N—N, N—O, O—N, O—O, S(O)$_p$—O, O—S(O)$_p$, or S(O)$_p$—S(O)$_p$ group and Z, U$^a$, Y$^a$, and Z$^a$ form other than a biphenyl group;

R$^1$ is Q, —C$_{1-6}$ alkylene-Q, —C$_{2-6}$ alkenylene-Q, —C$_{2-6}$ alkynylene-Q, —(CR$^a$R$^{a1}$)$_r$O(CR$^a$R$^{a1}$)$_s$-Q, —(CR$^a$R$^{a1}$)$_r$NR$^a$(CR$^a$R$^{a1}$)$_s$-Q, —(CR$^a$R$^{a1}$)$_r$C(O)(CR$^a$R$^{a1}$)$_s$-Q, —(CR$^a$R$^{a1}$)$_r$C(O)O(CR$^a$R$^{a1}$)$_s$-Q, —(CR$^a$R$^{a1}$)$_r$OC(O)(CR$^a$R$^{a1}$)$_s$-Q, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$-Q, —(CR$^a$R$^{a1}$)$_r$NR$^a$C(O)(CR$^a$R$^{a1}$)$_s$-Q, —(CR$^a$R$^{a1}$)$_r$OC(O)O(CR$^a$R$^{a1}$)$_s$-Q, —(CR$^a$R$^{a1}$)$_r$OC(O)NR$^a$(CR$^a$R$^{a1}$)$_s$-Q, —(CR$^a$R$^{a1}$)$_r$NR$^a$C(O)O(CR$^a$R$^{a1}$)$_s$-Q, —(CR$^a$R$^{a1}$)$_r$NR$^a$C(O)NR$^a$(CR$^a$R$^{a1}$)$_s$-Q, —(CR$^a$R$^{a1}$)$_r$S(O)$_p$(CR$^a$R$^{a1}$)$_s$-Q, —(CR$^a$R$^{a1}$)$_r$SO$_2$NR$^a$(CR$^a$R$^{a1}$)$_s$-Q, —(CR$^a$R$^{a1}$)$_r$NR$^a$SO$_2$(CR$^a$R$^{a1}$)$_s$-Q, or —(CR$^a$R$^{a1}$)$_r$NR$^a$SO$_2$NR$^a$(CR$^a$R$^{a1}$)$_s$-Q;

R$^2$ is Q$^1$, —C$_{1-6}$ alkylene-Q$^1$, —C$_{2-6}$ alkenylene-Q$^1$, —C$_{2-6}$ alkynylene-Q$^1$, —(CR$^a$R$^{a1}$)$_r$O(CR$^a$R$^{a1}$)$_s$-Q$^1$, —(CR$^a$R$^{a1}$)$_r$NR$^a$(CR$^a$R$^{a1}$)$_s$-Q$^1$, —(CR$^a$R$^{a1}$)$_r$C(O)(CR$^a$R$^{a1}$)$_s$-Q$^1$, —(CR$^a$R$^{a1}$)$_r$C(O)O(CR$^a$R$^{a1}$)$_s$-Q$^1$, —(CR$^a$R$^{a1}$)$_r$OC(O)(CR$^a$R$^{a1}$)$_s$-Q$^1$, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$-Q$^1$, —(CR$^a$R$^{a1}$)$_r$NR$^a$C(O)(CR$^a$R$^{a1}$)$_s$-Q$^1$, —(CR$^a$R$^{a1}$)$_r$OC(O)O(CR$^a$R$^{a1}$)$_s$-Q$^1$, —(CR$^a$R$^{a1}$)$_r$OC(O)NR$^a$(CR$^a$R$^{a1}$)$_s$-Q$^1$, —(CR$^a$R$^{a1}$)$_r$NR$^a$C(O)NR$^a$(CR$^a$R$^{a1}$)$_s$-Q$^1$, —(CR$^a$R$^{a1}_2$)$_r$S(O)$_p$(CR$^a$R$^{a1}$)$_s$-Q$^1$, —(CR$^a$R$^{a1}$)$_r$SO$_2$NR$^a$(CR$^a$R$^{a1}$)$_s$-Q$^1$, —(CR$^a$R$^{a1}$)$_r$NR$^a$SO$_2$(CR$^a$R$^{a1}$)$_s$-Q$^1$, or —(CR$^a$R$^{a1}$)$_r$NR$^a$SO$_2$NR$^a$(CR$^a$R$^{a1}$)$_s$-Q$^1$;

R$^3$ is Q, —C$_{1-6}$ alkylene-Q, —C$_{2-6}$ alkenylene-Q, —C$_{2-6}$ alkynylene-Q, —(CR$^a$R$^{a1}$)$_r$O(CR$^a$R$^{a1}$)$_s$-Q, —(CR$^a$R$^{a1}$)$_r$NR$^a$(CR$^a$R$^{a1}$)$_s$-Q, —(CR$^a$R$^{a1}$)$_r$C(O)(CR$^a$R$^{a1}$)$_s$-Q, —(CR$^a$R$^{a1}$)$_r$C(O)O(CR$^a$R$^{a1}$)$_s$-Q, —(CR$^a$R$^{a1}$)$_r$OC(O)(CR$^a$R$^{a1}$)$_s$-Q, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$-Q, —(CR$^a$R$^{a1}$)$_r$NR$^a$C(O)(CR$^a$R$^{a1}$)$_s$-Q, —(CR$^a$R$^{a1}$)$_r$OC(O)O(CR$^a$R$^{a1}$)$_s$Q, —(CR$^a$R$^{a1}$)$_r$OC(O)NR$^a$(CR$^a$R$^{a1}$)$_s$-Q, —(CR$^a$R$^{a1}$)$_r$NR$^a$C(O)O(CR$^a$R$^{a1}$)$_s$-Q, —(CR$^a$R$^{a1}$)$_r$NR$^a$C(O)NR$^a$(CR$^a$R$^{a1}$)$_s$-Q, —(CR$^a$R$^{a1}$)$_r$S(O)$_p$(CR$^a$R$^{a1}$)$_s$-Q, —(CR$^a$R$^{a1}$)$_r$SO$_2$NR$^a$(CR$^a$R$^{a1}$)$_s$-Q, —(CR$^a$R$^{a1}$)$_r$NR$^a$SO$_2$(CR$^a$R$^{a1}$)$_s$-Q, or —(CR$^a$R$^{a1}$)$_r$NR$^a$SO$_2$NR$^a$(CR$^a$R$^{a1}$)$_s$-Q;

each Q is, independently at each occurrence, H, CHF$_2$, CH$_2$F, CF$_3$, a C$_{3-13}$ carbocycle substituted with 0–5 R$^d$, or a 5–14 membered heterocycle consisting of carbon atoms and 1–4 heteroatoms selected from N, O, and S(O)$_p$, and substituted with 0–5 R$^d$;

each Q$^1$ is, independently at each occurrence, H, a C$_{3-13}$ carbocycle substituted with 0–5 R$^d$, or a 5–14 membered heterocycle consisting of carbon atoms and 1–4 heteroatoms selected from N, O, and S(O)$_p$, and substituted with 0–5 R$^d$;

each R$^a$ is, independently at each occurrence, H, C$_{1-6}$ alkyl, phenyl, or benzyl;

each R$^{a1}$ is, independently at each occurrence, H, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, or —(CH$_2$)$_r$-3–8 membered carbocyclic or heterocyclic ring consisting of carbon atoms and 0–2 ring heteroatoms selected from N, NR$^{a2}$, O, and S(O)$_p$, and substituted with 0–3 R$^{c1}$;

alternatively, R$^a$ and R$^{a1}$ when attached to a nitrogen, together with the nitrogen to which they are attached, combine to form a 5 or 6 membered heterocycle consisting of carbon atoms and from 0–1 additional heteroatoms selected from N, NR$^{a2}$, O, and S(O)$_p$;

each R$^{a2}$ is, independently at each occurrence, C$_{1-4}$ alkyl, phenyl, or benzyl;

each R$^b$ is, independently at each occurrence, C$_{1-6}$ alkyl substituted with 0–1 R$^{c1}$, OR$^a$, SR$^a$, Cl, F, Br, I, =O, CN, NO$_2$, —NR$^a$R$^{a1}$, —C(O)R$^a$, —C(O)OR$^a$, —C(O)NR$^a$R$^{a1}$, —C(S)NR$^a$R$^{a1}$, —NR$^a$C(O)NR$^a$R$^{a1}$, —OC(O)NR$^a$R$^{a1}$, —NR$^a$C(O)OR$^a$, —S(O)$_2$NR$^a$R$^{a1}$, —NR$^a$S(O)$_2$R$^{a3}$, —NR$^a$S(O)$_2$NR$^a$R$^{a1}$, —OS(O)$_2$NR$^a$R$^{a1}$, —S(O)$_p$R$^{a3}$, CF$_3$, —CF$_2$CF$_3$, CHF$_2$, CH$_2$F, or phenyl;

each R$^{a3}$ is, independently at each occurrence, H, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, or —(CH$_2$)$_r$-3–8 membered carbocyclic or heterocyclic ring consisting of carbon atoms and 0–2 ring heteroatoms selected from N, NR$^{a2}$, O, and S(O)$_p$, and substituted with 0–3 R$^{c1}$;

each R$^c$ is, independently at each occurrence, H, OR$^a$, Cl, F, Br, I, =O, CN, NO$_2$, CF$_3$, —CF$_2$CF$_3$, CH$_2$F, CHF$_2$, —(CR$^a$R$^{a1}$)$_r$NR$^a$R$^{a1}$, —(CR$^a$R$^{a1}$)$_r$C(=NCN)NR$^a$R$^{a1}$, —(CR$^a$R$^{a1}$)$_r$C(=NR$^a$)NR$^a$R$^{a1}$, —(CR$^a$R$^{a1}$)$_r$C(=NOR$^a$)NR$^a$R$^{a1}$, —(CR$^a$R$^{a1}$)$_r$C(O)NR$^a$OH, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(S)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$C(S)NR$^a$R$^{a1}$, —(CR$^a$R$^{a1}$)$_r$OC(O)NR$^a$R$^{a1}$, —(CR$^a$R$^{a1}$)$_r$NR$^a$C(O)OR$^{a1}$, —(CR$^a$R$^{a1}$)$_r$NR$^a$C(O)NR$^a$R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, —(CR$^a$R$^{a1}$)$_r$NR$^a$SO$_2$NR$^a$R$^{a1}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$^a$R$^{a1}$)$_r$—C$_{3-10}$ carbocycle substituted with 0–2 R$^{c1}$, or —(CR$^a$R$^{a1}$)$_r$-5–14 membered heterocycle consisting of carbon atoms and 1–4 heteroatoms selected from N, O, and S(O)$_p$, and substituted with 0–2 R$^{c1}$;

alternatively, when two R$^c$ groups are attached to the same carbon atom, they form a 3–8 membered carbocyclic or heterocyclic spiro ring C substituted with 0–2 R$^{c1}$ and consisting of carbon atoms, 0–4 ring heteroatoms selected from O, N, and S(O)$_p$, and 0–2 double bonds, provided that ring C contains other than a S—S, O—O, or S—O bond;

alternatively, when two R$^c$ groups are attached to adjacent carbon atoms, together with the carbon atoms to which they are attached they form a 5–7 membered carbocyclic or heterocyclic ring D substituted with 0–2 R$^{c1}$ and consisting of: carbon atoms and 0–2 heteroatoms selected from N, O, and S(O)$_p$;

each $R^{c1}$ is, independently at each occurrence, H, $C_{1-4}$ alkyl, $OR^a$, Cl, F, Br, I, =O, $CF_3$, —CN, $NO_2$, $C(O)R^a$, $C(O)OR^a$, $C(O)NR^aR^a$, or $S(O)_pR^a$;

each $R^d$ is, independently at each occurrence, $C_{1-6}$ alkyl, $OR^a$, Cl, F, Br, I, =O, CN, $NO_2$, —$NR^aR^{a1}$, —$C(O)R^a$, —$C(O)OR^a$, —$C(O)NR^aR^{a1}$, —$C(S)NR^aR^{a1}$, —$NR^aC(O)NR^aR^{a1}$, —$OC(O)NR^aR^{a1}$, —$NR^aC(O)O$, —$S(O)_2NR^aR^{a1}$, —$NR^aS(O)_2R^{3a}$, —$NR^aS(O)_2NR^aR^{a1}$, —$OS(O)_2NR^aR^{a1}$, —$S(O)_pR^{a3}$, $CF_3$, $CF_2CF_3$, $C_{3-10}$ carbocycle, or a 5–14 membered heterocycle consisting of carbon atoms and 1–4 heteroatoms selected from N, O, and $S(O)_p$;

each $R^5$ is, independently at each occurrence, $C_{1-10}$ alkyl substituted with 0–2 $R^b$, or $C_{1-8}$ alkyl substituted with 0–2 $R^e$;

each $R^e$ is, independently at each occurrence, phenyl substituted with 0–2 $R^b$ or biphenyl substituted with 0–2 $R^b$;

each $R^6$ is, independently at each occurrence, phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, or —$CH(R^8)OC(=O)OR^9$;

$R^7$ is H, $C_{1-10}$ alkyl, $C_{2-6}$ alkenyl, $C_{3-6}$ cycloalkyl-$C_3$ alkyl-, or phenyl-$C_{1-6}$ alkyl-;

$R^{7a}$ is H, $C_{1-10}$ alkyl, $C_{2-6}$ alkenyl, $C_{3-6}$ cycloalkyl-$C_{1-3}$ alkyl-, or phenyl-$C_{1-6}$ alkyl-;

each $R^8$ is, independently at each occurrence, H or $C_{1-4}$ linear alkyl;

each $R^9$ is, independently at each occurrence, H, $C_{1-8}$ alkyl substituted with 1–2 $R^f$, $C_{3-8}$ cycloalkyl substituted with 1-2 $R^f$, or phenyl substituted with 0–2 $R^b$;

each $R^f$ is, independently at each occurrence, $C_{1-4}$ alkyl, $C_{3-8}$ cycloalkyl, $C_{1-5}$ alkoxy, or phenyl substituted with 0–2 $R^b$;

m, at each occurrence, is selected from 0, 1, 2 and 3;

p, at each occurrence, is selected from 0, 1, and 2;

r, at each occurrence, is selected from 0, 1, 2, 3, and 4;

s, at each occurrence, is selected from 0, 1, 2, 3, and 4; and t, at each occurrence, is selected from 1, 2, 3, and 4.

In some embodiments according to the first aspect, the present invention includes compounds of Formula (I) where A is —C(O)NHOH or —N(OH)CHO. In other embodiments, A is —C(O)NHOH.

In some embodiments according to the first aspect, the present invention includes compounds of Formula (I) where ring B is substituted with 0–3 $R^3$ and is a 4–8 membered ring consisting of carbon atoms, 0–3 heteroatoms selected from N, O, and $S(O)_p$, 0–1 additional carbonyl groups, and 0–2 double bonds. In other embodiments, ring B is substituted with 0–2 $R^3$ and is a 4–7 membered ring consisting of carbon atoms, 0–3 heteroatoms selected from N, O, and $S(O)_p$, 0–1 additional carbonyl groups, and 0–2 double bonds. In other embodiments, ring B is substituted with 0–2 $R^3$ and is a 5–6 membered ring consisting of carbon atoms, 0–2 heteroatoms selected from N, O, and $S(O)_p$, 0–1 additional carbonyl groups, and 0–1 double bonds.

In some embodiments according to the first aspect, the present invention includes compounds of Formula (I) where U is absent or is O, $NR^{a1}$, C(O), $CR^a(OH)$, $C(O)O$, $OC(O)$, $C(O)NR^{a1}$, $NR^{a1}C(O)$, $S(O)_p$, $S(O)_pNR^{a1}$, or $NR^{a1}S(O)_p$. In other embodiments, U is absent or is O, $NR^{a1}$, C(O), $C(O)NR^{a1}$, $NR^{a1}C(O)$, $S(O)_p$, $S(O)_pNR^{a1}$, or $NR^{a1}S(O)_p$. In other embodiments, U is absent.

In some embodiments according to the first aspect, the present invention includes compounds of Formula (I) where X is absent or is $C_{1-3}$ alkylene. In other embodiments, X is absent or is methylene. In other embodiments, X is absent. In other embodiments, X is methylene.

In some embodiments according to the first aspect, the present invention includes compounds of Formula (I) where $U^a$ is absent or is O, $NR^{a1}$, C(O), $CR^a(OH)$, C(O)O, OC(O), $C(O)NR^{a1}$, $NR^{a1}C(O)$, $S(O)_p$, $S(O)_pNR^{a1}$, or $NR^{a1}S(O)_p$. In other embodiments, $U^a$ is absent or is O, $NR^{a1}$, C(O), $C(O)NR^{a1}$, $NR^{a1}C(O)$, $S(O)_p$, $S(O)_pNR^{a1}$, or $NR^{a1}S(O)_p$. In other embodiments, $U^a$ is absent or is O. In other embodiments, $U^a$ is O.

In some embodiments according to the first aspect, the present invention includes compounds of Formula (I) where $X^a$ is absent or is $C_{1-4}$ alkylene, $C_{2-4}$ alkenylene, or $C_{2-4}$ alkynylene. In other embodiments, $X^a$ is methylene.

In some embodiments according to the first aspect, the present invention includes compounds of Formula (I) where $Y^a$ is absent or is O or $NR^{a1}$. In other embodiments, $Y^a$ is absent or is O. In other embodiments, $Y^a$ is O.

In some embodiments according to the first aspect, the present invention includes compounds of Formula (I) where $R^1$ is Q, —$C_{1-6}$ alkylene-Q, —$C_{2-6}$ alkenylene-Q, —$C_{2-6}$ alkynylene-Q, —$(CR^aR^{a1})_rO(CR^aR^{a1})_s$-Q, —$(CR^aR^{a1})_tNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_tNR^aC(O)(CR^aR^{a1})_s$-Q, —$(CR^aR^{a1})_rS(CR^aR^{a1})_s$-Q, —$(CR^aR^{a1})_rS(O)(CR^aR^{a1})_s$-Q, —$(CR^aR^{a1})_rS(O)_2(CR^aR^{a1})_s$-Q, —$(CR^aR^{a1})_rSO_2NR^a(CR^aR^{a1})_s$-Q, or —$(CR^aR^{a1})_tNR^aSO_2(CR^aR^{a1})_s$-Q. In other embodiments, $R^1$ is Q, —$C_{1-6}$ alkylene-Q, —$C_{2-6}$ alkenylene-Q, —$C_{2-6}$ alkynylene-Q, —$(CH_2)_rO(CH_2)_s$-Q, —$(CH_2)_rNR^a(CH_2)_s$-Q, —$(CH_2)_rC(O)(CH_2)_s$-Q, —$(CH_2)_rC(O)O(CH_2)_s$-Q, —$(CH_2)_rC(O)NR^aR^{a1}$, —$(CH_2)_rC(O)NR^a(CH_2)_s$-Q, —$(CH_2)_rS(CH_2)_s$-Q, —$(CH_2)_rS(O)(CH_2)_s$-Q, —$(CH_2)_rS(O)_2(CH_2)_s$-Q, —$(CH_2)_rSO_2NR^a(CH_2)_s$-Q, or —$(CH_2)_tNR^aSO_2(CH_2)_s$-Q. In other embodiments, $R^1$ is Q, —$C_{1-6}$ alkylene-Q, —$C_{2-6}$ alkenylene-Q, or —$C_{2-6}$ alkynylene-Q. In other embodiments, $R^1$ is H or $C_{1-4}$ alkyl. In other embodiments, $R^1$ is H or Me.

In some embodiments according to the first aspect, the present invention includes compounds of Formula (I) where $R^2$ is $Q^1$, —$C_{1-6}$ alkylene-$Q^1$, —$C_{2-6}$ alkenylene-$Q^1$, —$C_{2-6}$ alkynylene-$Q^1$, —$(CR^aR^{a1})_rO(CR^aR^{a1})_s$-$Q^1$, —$(CR^aR^{a1})_tNR^a(CR^aR^{a1})_s$-$Q^1$, —$(CR^aR^{a1})_rC(O)(CR^aR^{a1})_s$-$Q^1$, —$(CR^aR^{a1})_rC(O)O(CR^aR^{a1})_s$-$Q^1$, —$(CR^aR^{a1})_rOC(O)(CR^aR^{a1})_s$-$Q^1$, —$(CR^aR^{a1})_rC(O)NR^aR^{a1}$, —$(CR^aR^{a1})_rC(O)NR^a(CR^aR^{a1})_s$-$Q^1$, —$(CR^aR^{a1})_rNR^aC(O)(CR^aR^{a1})_s$-$Q^1$, —$(CR^aR^{a1}_2)_rS(O)_p(CR^aR^{a1})_s$-$Q^1$, —$(CR^aR^{a1})_rSO_2NR^a(CR^aR^{a1})_s$-$Q_1$, or —$(CR^aR^{a1})_rNR^aSO_2(CR^aR^{a1})_s$-$Q^1$. In other embodiments, $R^2$ is $Q^1$, —$C_{1-6}$ alkylene-$Q^1$, —$C_{2-6}$ alkenylene-$Q^1$, —$C_{2-6}$ alkynylene-$Q^1$, —$(CR^aR^{a1})_rO(CR^aR^{a1})_s$-$Q^1$, —$(CR^aR^{a1})_rNR^a(CR^aR^{a1})_s$-$Q^1$, —$(CR^aR^{a1})_r C(O)(CR^aR^{a1})_s$-$Q^1$, —$(CR^aR^{a1})_rC(O)O(CR^aR^{a1})_s$-$Q^1$, —$(CR^aR^{a1})_rOC(O)(CR^aR^{a1})_s$-$Q^1$, —$(CR^aR^{a1})_rC(O)NR^aR^{a1}$, —$(CR^aR^{a1})_rC(O)NR^a(CR^aR^{a1})_s$-$Q^1$, —$(CR^aR^{a1})_rNR^aC(O)(CR^aR^{a1})_s$-$Q^1$, —$(CR^aR^{a1}_2)_rS(O)_p(CR^aR^{a1})_s$-$Q^1$, —$(CR^aR^{a1})_rSO_2NR^a(CR^aR^{a1})_s$-$Q^1$, or —$(CR^aR^{a1})_rNR^aSO_2(CR^aR^{a1})_s$-$Q^1$. In other embodiments, $R^2$ is $Q$, —$C_{1-6}$ alkylene-$Q^1$, —$C_{2-6}$ alkenylene-$Q^1$, —$C_{2-6}$ alkynylene-$Q^1$, —$(CH_2)_rO(CH_2)_s$-$Q^1$, —$(CH_2)_rNR^a(CH_2)_s$-$Q^1$, —$(CH_2)_rC(O)(CH_2)_s$-$Q^1$, —$(CH_2)_rC(O)O(CH_2)_s$-$Q^1$, —$(CH_2)_rC(O)NR^aR^{a1}$, —$(CH_2)_rC(O)NR^a (CH$_2$)$_s$-Q$^1$, —(CH$_2$)$_r$S(CH$_2$)$_s$-Q$^1$, —(CH$_2$)$_r$S(O)(CH$_2$)$_s$-Q$^1$, —(CH$_2$)$_r$S(O)$_2$(CH$_2$)$_s$-Q$^1$, —(CH$_2$)$_r$SO$_2$NR$^a$(CH$_2$)$_s$-Q$^1$, or —(CH$_2$)$_r$NR$^a$SO$_2$(CH$_2$)$_s$-Q$^1$;.

In some embodiments according to the first aspect, the present invention includes compounds of Formula (I) where R$^3$ is Q, —C$_{1-6}$ alkylene-Q, —C$_{2-6}$ alkenylene-Q, —C$_{2-6}$ alkynylene-Q, —(CR$^a$R$^{a1}$)$_r$O(CR$^a$R$^{a1}$)$_s$-Q, —(CR$^a$R$^{a1}$)$_r$NR$^a$(CR$^a$R$^{a1}$)$_s$-Q, —(CR$^a$R$^{a1}$)$_r$C(O)(CR$^a$R$^{a1}$)$_s$-Q, —(CR$^a$R$^{a1}$)$_r$C(O)O(CR$^a$R$^{a1}$)$_s$-Q, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$-Q, —(CR$^a$R$^{a1}$)$_r$NR$^a$C(O)(CR$^a$R$^{a1}$)$_s$-Q, —(CR$^a$R$^{a1}$)$_r$S(O)$_p$(CR$^a$R$^{a1}$)$_s$-Q, —(CR$^a$R$^{a1}$)$_r$SO$_2$NR$^a$(CR$^a$R$^{a1}$)$_s$-Q, or —(CR$^a$R$^{a1}$)$_r$NR$^a$SO$_2$(CR$^a$R$^{a1}$)$_s$-Q. In other embodiments, R$^3$ is Q, —C$_{1-6}$ alkylene-Q, —C$_{2-6}$ alkenylene-Q, —C$_{2-6}$ alkynylene-Q, —(CH$_2$)$_r$O(CH$_2$)$_s$-Q, —(CH$_2$)$_r$NR$^a$(CH$_2$)$_s$-Q, —(CH$_2$)$_r$C(O)(CH$_2$)$_s$-Q, —(CH$_2$)$_r$C(O)O(CH$_2$)$_s$-Q, —(CH$_2$)$_r$C(O)NR$^a$R$^{a1}$, —(CH$_2$)$_r$C(O)NR$^a$(CH$_2$)$_s$-Q, —(CH$_2$)$_r$NR$^a$C(O)(CH$_2$)$_s$-Q, —(CH$_2$)$_r$S(O)$_p$(CH$_2$)$_s$-Q, —(CH$_2$)$_r$SO$_2$NR$^a$(CH$_2$)$_s$-Q, or —(CH$_2$)$_r$NR$^a$SO$_2$(CH$_2$)$_s$-Q. In other embodiments, R$^3$ is H, C$_{1-4}$ alkyl, C$_{2-4}$ alkenyl, C$_{2-4}$ alkynyl, phenyl, or benzyl.

In some embodiments according to the first aspect, the present invention includes compounds of Formula (I) where each Q is, independently at each occurrence, H, CHF$_2$, CH$_2$F, CF$_3$, a C$_{3-13}$ carbocycle substituted with 0–3 R$^d$, or a 5–14 membered heterocycle consisting of carbon atoms and 1–4 heteroatoms selected from N, O, and S(O)$_p$, and substituted with 0–3 R$^d$. In other embodiments, each Q is, independently at each occurrence, H, a C$_{3-8}$ carbocycle substituted with 0–3 R$^d$, or a 5–10 membered heterocycle consisting of carbon atoms and 1–4 heteroatoms selected from N, O, and S(O)$_p$, and substituted with 0–3 R$^d$. In other embodiments, Q is, independently at each occurrence, H, phenyl substituted with 0–2 R$^d$, or a 5–6 membered heterocycle consisting of carbon atoms and 1–4 heteroatoms selected from the group consisting of N, O, and S(O)$_p$, and substituted with 0–2 R$^d$.

In some embodiments according to the first aspect, the present invention includes compounds of Formula (I) where Q$^1$ is H, a C$_{3-6}$ cycloalkyl substituted with 0–2 R$^d$, phenyl substituted with 0–3 R$^d$ or a 5–6 membered heterocycle consisting of carbon atoms and 1–4 heteroatoms selected from the group consisting of N, O, and S(O)$_p$, and substituted with 0–3 R$^d$. In other embodiments, Q$^1$ is, independently at each occurrence, H, phenyl substituted with 0–2 R$^d$, or a 5–6 membered heterocycle consisting of carbon atoms and 1–4 heteroatoms selected from the group consisting of N, O, and S(O)$_p$, and substituted with 0–2 R$^d$.

In some embodiments according to the first aspect, the present invention includes compounds of Formula (I) Z is a C$_{3-8}$ cycloalkyl substituted with 0–5 R$^b$, a C$_{3-8}$ cycloalkenyl substituted with 0–5 R$^b$, phenyl substituted with 0–4 R$^b$, naphthyl substituted with 0–5 R$^b$, or a 5–14 membered heterocycle consisting of carbon atoms and 1–4 heteroatoms selected from the group consisting of N, O, and S(O)$_p$ and substituted with 0–5 R$^b$. In other embodiments, Z is a C$_{4-8}$ cycloalkyl substituted with 0–3 R$^b$, a C$_{4-8}$ cycloalkenyl substituted with 0–3 R$^b$, phenyl substituted with 0–4 R$^b$, naphthyl substituted with 0–5 R$^b$, or a heterocycle substituted with 0–3 R$^b$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, and quinazolinyl. In other embodiments, Z is phenyl substituted with 0–3 R$^b$ or a heterocycle substituted with 0–2 R$^b$ and selected from the group: thienyl, furanyl, pyridyl, pyrazinyl, pyrimidinyl, thiazolyl, oxazolyl, isoxazolyl, and imidazolyl. In other embodiments, Z is phenyl substituted with 0–4 R$^b$, thienyl substituted with 0–2 R$^b$, thiazolyl substituted with 0–1 R$^b$, oxazolyl substituted with 0–1 R$^b$, isoxazolyl substituted with 0–1 R$^b$, or imidazolyl substituted with 0–1 R$^b$. In other embodiments, Z is phenyl substituted with 0–1 R$^b$.

In some embodiments according to the first aspect, the present invention includes compounds of Formula (I) where Z$^a$ is a C$_{5-10}$ carbocycle substituted with 0–5 R$^c$ or a 5–14 membered heterocycle consisting of carbon atoms and 1–4 heteroatoms selected from N, O, and S(O)$_p$, and substituted with 0–5 R$^c$. In other embodiments, Z$^a$ is phenyl substituted with 0–3 R$^c$, naphthyl substituted with 0–3 R$^c$, or a heterocycle substituted with 0–3 R$^c$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolo[1,5-a]pyridinyl. In other embodiments, Z$^a$ is phenyl substituted with 0–3 R$^c$, naphthyl substituted with 0–3 R$^c$, or a heterocycle substituted with 0–3 R$^c$ and selected from the group: pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, pyrazolyl, and pyrazolo[1,5-a]pyridinyl. In other embodiments, Z$^a$ is quinolinyl substituted with 0–3 R$^c$.

In a second aspect, the present invention includes compounds of Formula (I) or a stereoisomer or pharmaceutically acceptable salt or solvate form thereof, wherein:

ring B is substituted with 0–3 R$^3$ and is a 4–8 membered ring consisting of carbon atoms, 0–3 heteroatoms selected from N, O, and S(O)$_p$, 0–1 additional carbonyl groups, and 0–2 double bonds;

U is absent or is O, NR$^{a1}$, C(O), CR$^a$(OH), C(O)O, OC(O), C(O)NR$^{a1}$, NR$^{a1}$C(O), S(O)$_p$, S(O)$_p$NR$^{a1}$, or NR$^{a1}$S(O)$_p$;

X is absent or is C$_{1-3}$ alkylene;

U$^a$ is absent or is O, NR$^{a1}$, C(O), CR$^a$(OH), C(O)O, C(O)NR$^{a1}$, NR$^{a1}$C(O), S(O)$_p$, S(O)$_p$NR$^{a1}$, or NR$^{a1}$S(O)$_p$;

X$^a$ is absent or is C$_{1-4}$ alkylene, C$_{2-4}$ alkenylene, or C$_{2-4}$ alkynylene;

Y$^a$ is absent or is O or NR$^{a1}$;

R$^1$ is Q, —C$_{1-6}$ alkylene-Q, —C$_{2-6}$ alkenylene-Q, —C$_{2-6}$ alkynylene-Q, —(CR$^a$R$^{a1}$)$_r$O(CR$^a$R$^{a1}$)$_s$-Q, —(CR$^a$R$^{a1}$)$_r$NR$^a$(CR$^a$R$^{a1}$)$_s$-Q, —(CR$^a$R$^{a1}$)$_r$C(O)(CR$^a$R$^{a1}$)$_s$-Q, —(CR$^a$R$^{a1}$)$_r$C(O)O(CR$^a$R$^{a1}$)$_s$-Q, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$-Q, —(CR$^a$R$^{a1}$)$_r$S $(O)_p(CR^aR^{a1})_s$-Q, —$(CR^aR^{a1})_r SO_2 NR^a (CR^aR^{a1})_s$-Q, or —$(CR^aR^{a1})_r NR^a SO_2 (CR^aR^{a1})_s$-Q;

$R^2$ is $Q^1$, $C_{1-6}$ alkylene-$Q^1$, $C_{2-6}$ alkenylene-$Q^1$, $C_{2-6}$ alkynylene-$Q^1$, —$(CR^aR^{a1})_r O(CR^aR^{a1})_s$-$Q^1$, —$(CR^aR^{a1})_r NR^a(CR^aR^{a1})_s$-$Q^1$, —$(CR^aR^{a1})_r C(O)(CR^aR^{a1})_s$-$Q^1$, —$(CR^aR^{a1})_r C(O)O(CR^aR^{a1})_s$-$Q^1$, —$(CR^aR^{a1})_r OC(O)(CR^aR^{a1})_s$-$Q^1$, —$(CR^aR^{a1})_r C(O)NR^aR^{a1}$, —$(CR^aR^{a1})_r C(O)NR^a(CR^aR^{a1})_s$-$Q^1$, —$(CR^aR^{a1})_r NR^a C(O)(CR^aR^{a1})_s$-$Q^1$, —$(CR^aR^{a1}_2)_r S(O)_p(CR^aR^{a1})_s$-$Q^1$, —$(CR^aR^{a1})_r SO_2 NR^a(CR^aR^{a1})_s$-$Q^1$, or —$(CR^aR^{a1})_r NR^a SO_2(CR^aR^{a1})_s$-$Q^1$;

$R^3$ is Q, —$C_{1-6}$ alkylene-Q, —$C_{2-6}$ alkenylene-Q, —$C_{2-6}$ alkynylene-Q, —$(CR^aR^{a1})_r O(CR^aR^{a1})_s$-Q, —$(CR^aR^{a1})_r NR^a(CR^aR^{a1})_s$-Q, —$(CR^aR^{a1})_r C(O)(CR^aR^{a1})_s$-Q, —$(CR^aR^{a1})_r C(O)O(CR^aR^{a1})_s$-Q, —$(CR^aR^{a1})_r C(O)NR^aR^{a1}$, —$(CR^aR^{a1})_r C(O)NR^a(CR^aR^{a1})_s$-Q, —$(CR^aR^{a1})_r NR^a C(O)(CR^aR^{a1})_s$-Q, —$(CR^aR^{a1})_r S(O)_p(CR^aR^{a1})_s$-Q, —$(CR^aR^{a1})_r SO_2 NR^a(CR^aR^{a1})_s$-Q, or —$(CR^aR^{a1})_r NR^a SO_2(CR^aR^{a1})_s$-Q;

each Q is, independently at each occurrence, H, $CHF_2$, $CH_2F$, $CF_3$, a $C_{3-13}$ carbocycle substituted with 0–3 $R^d$, or a 5–14 membered heterocycle consisting of carbon atoms and 1–4 heteroatoms selected from N, O, and $S(O)_p$, and substituted with 0–3 $R^d$;

each $R^a$ is, independently at each occurrence, H, $C_{1-6}$ alkyl, phenyl, or benzyl;

each $R^{a1}$ is, independently at each occurrence, H, $C_{1-6}$ alkyl, $C_{2-6}$ alkenyl, $C_{2-6}$ alkynyl, or —$(CH_2)_r$-3–8 membered carbocyclic or heterocyclic ring consisting of carbon atoms and 0–2 ring heteroatoms selected from N, $NR^{a2}$, O, and $S(O)_p$;

alternatively, $R^a$ and $R^{a1}$ when attached to a nitrogen, together with the nitrogen to which they are attached, combine to form a 5 or 6 membered heterocycle consisting of carbon atoms and from 0–1 additional heteroatoms selected from N, $NR^{a2}$, O, and $S(O)_p$;

each $R^c$ is, independently at each occurrence, H, $OR^a$, Cl, F, Br, =O, CN, $NO_2$, $CF_3$, $CH_2F$, $CHF_2$, —$CF_2 CF_3$, —$(CR^aR^{a1})_r NR^aR^{a1}$, —$(CR^aR^{a1})_r C(O)R^{a1}$, —$(CR^aR^{a1})_r C(O)OR^{a1}$, —$(CR^aR^{a1})_r C(O)NR^aR^{a1}$, —$(CR^aR^{a1})_r NR^a C(O)R^{a1}$, —$(CR^aR^{a1})_r S(O)_p R^{a3}$, —$(CR^aR^{a1})_r SO_2 NR^aR^{a1}$, —$(CR^aR^{a1})_r NR^a SO_2 R^{a3}$, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, —$(CH_2)_r$—$C_{3-6}$ carbocycle substituted with 0–2 $R^{c1}$, or —$(CH_2)_r$-5–6 membered heterocycle consisting of carbon atoms and 1–4 heteroatoms selected from N, O, and $S(O)_p$, and substituted with 0–2 $R^{c1}$;

alternatively, when two $R^c$ groups are attached to the same carbon atom, they form a 3–8 membered carbocyclic or heterocyclic spiro ring C substituted with 0–2 $R^{c1}$ and consisting of carbon atoms, 0–4 ring heteroatoms selected from O, N, and $S(O)_p$, and 0–2 double bonds, provided that ring C contains other than a S—S, O—O, or S—O bond;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of: carbon atoms and 0–2 heteroatoms selected from N, O, and $S(O)_p$;

each $R^d$ is, independently at each occurrence, $C_{1-6}$ alkyl, $OR^a$, Cl, F, Br, =O, —CN, $NO_2$, —$NR^aR^{a1}$, —$C(O)R^a$, —$C(O)OR^a$, —$C(O)NR^aR^{a1}$, —$S(O)_2 NR^aR^{a1}$, —$NR^a S(O)_2 NR^aR^{a1}$, —$S(O)_p R^{a3}$, $CF_3$, $C_{3-6}$ carbocycle or a 5–6 membered heterocycle consisting of carbon atoms and 1–4 heteroatoms selected from N, O, and $S(O)_p$;

each $R^5$ is, independently at each occurrence, $C_{1-6}$ alkyl substituted with 0–2 $R^b$, and $C_{1-4}$ alkyl substituted with 0–2 $R^e$;

each $R^9$ is, independently at each occurrence, H, $C_{1-6}$ alkyl substituted with 1–2 $R^f$, $C_{3-6}$ cycloalkyl substituted with 1–2 $R^f$, or phenyl substituted with 0–2 $R^b$; and each $R^f$ is, independently at each occurrence, $C_{1-4}$ alkyl, $C_{3-6}$ cycloalkyl, $C_{1-5}$ alkoxy, or phenyl substituted with 0–2 $R^b$.

In a third aspect, the present invention includes compounds of Formula (I) or a stereoisomer or pharmaceutically acceptable salt or solvate form thereof, wherein:

A is —C(O)NHOH or —N(OH)CHO;

ring B is substituted with 0–2 $R^3$ and is a 4–7 membered ring consisting of carbon atoms, 0–3 heteroatoms selected from N, O, and $S(O)_p$, 0–1 additional carbonyl groups, and 0–2 double bonds;

U is absent or is O, $NR^{a1}$, C(O), $C(O)NR^{a1}$, $NR^{a1}C(O)$, $S(O)_p$, $S(O)_p NR^{a1}$, or $NR^{a1}S(O)_p$;

X is absent or is methylene or ethylene;

Z is a $C_{3-8}$ cycloalkyl substituted with 0–5 $R^b$, a $C_{3-8}$ cycloalkenyl substituted with 0–5 $R^b$, phenyl substituted with 0–5 $R^b$, naphthyl substituted with 0–5 $R^b$, or a 5–14 membered heterocycle consisting of carbon atoms and 1–4 heteroatoms selected from N, O, and $S(O)_p$, and substituted with 0–5 $R^b$;

$Z^a$ is a $C_{5-10}$ carbocycle substituted with 0–5 $R^c$ or a 5–14 membered heterocycle consisting of carbon atoms and 1–4 heteroatoms selected from N, O, and $S(O)_p$, and substituted with 0–5 $R^c$;

$R^1$ is Q, —$C_{1-6}$ alkylene-Q, —$C_{2-6}$ alkenylene-Q, —$C_{2-6}$ alkynylene-Q, —$(CH_2)_r O(CH_2)_s$-Q, —$(CH_2)_r NR^a(CH_2)_s$-Q, —$(CH_2)_r C(O)(CH_2)_s$-Q, —$(CH_2)_r C(O)O(CH_2)_s$-Q, —$(CH_2)_r C(O)NR^aR^{a1}$, —$(CH_2)_r C(O)NR^a(CH_2)_s$-Q, —$(CH_2)_r NR^a C(O)(CH_2)_s$-Q, —$(CH_2)_r S(O)_p(CH_2)_s$-Q, —$(CH_2)_r SO_2 NR^a(CH_2)_s$-Q, or —$(CH_2)_r NR^a SO_2(CH_2)_s$-Q;

$R^2$ is $Q^1$, —$C_{1-6}$ alkylene-$Q^1$, —$C_{2-6}$ alkenylene-$Q^1$, —$C_{2-6}$ alkynylene-$Q^1$, —$(CR^aR^{a1})_r O(CR^aR^{a1})_s$-$Q^1$, —$(CR^aR^{a1})_r NR^a(CR^aR^{a1})_s$-$Q^1$, —$(CR^aR^{a1})_r C(O)(CR^aR^{a1})_s$-$Q^1$, —$(CR^aR^{a1})_r C(O)O(CR^aR^{a1})_s$-$Q^1$, —$(CR^aR^{a1})_r C(O)NR^a(CR^aR^{a1})_s$-$Q^1$, —$(CR^aR^{a1})_r NR^a C(O)(CR^aR^{a1})_s$-$Q^1$, —$(CR^aR^{a1}_2)_r S(O)_p(CR^aR^{a1})_s$-$Q^1$, —$(CR^aR^{a1})_r SO_2 NR^a(CR^aR^{a1})_s$-$Q^1$, or —$(CR^aR^{a1})_r NR^a SO_2(CR^aR^{a1})_s$-$Q^1$;

$R^3$ is Q, —$C_{1-6}$ alkylene-Q, —$C_{2-6}$ alkenylene-Q, —$C_{2-6}$ alkynylene-Q, —$(CH_2)_r O(CH_2)_s$-Q, —$(CH_2)_r NR^a(CH_2)_s$-Q, —$(CH_2)_r C(O)(CH_2)_s$-Q, —$(CH_2)_r C(O)O(CH_2)_s$-Q, —$(CH_2)_r C(O)NR^aR^{a1}$, —$(CH_2)_r C(O)NR^a(CH_2)_s$-Q, —$(CH_2)_r NR^a C(O)(CH_2)_s$-Q, —$(CH_2)_r S(O)_p(CH_2)_s$-Q, —$(CH_2)_r SO_2 NR^a(CH_2)_s$-Q, or —$(CH_2)_r NR^a SO_2(CH_2)_s$-Q;

each Q is, independently at each occurrence, H, a $C_{3-8}$ carbocycle substituted with 0–3 $R^d$, or a 5–10 membered heterocycle consisting of carbon atoms and 1–4 heteroatoms selected from N, O, and $S(O)_p$, and substituted with 0–3 $R^d$;

each $R^{a3}$ is, independently at each occurrence, H, $C_{1-6}$ alkyl, $C_{2-6}$ alkenyl, or —$(CH_2)_r$-3–8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

each $R^c$ is, independently at each occurrence, H, $OR^a$, Cl, F, Br, =O, $CF_3$, $CH_2F$, $CHF_2$, —$(CR^aR^{a1})_r NR^aR^{a1}$, —$(CR^aR^{a1})_r C(O)R^{a1}$, —$(CR^aR^{a1})_r C(O)OR^{a1}$, —$(CR^aR^{a1})_r C(O)NR^aR^{a1}$, —$(CR^aR^{a1})_r NR^a C(O)R^{a1}$, —$(CR^aR^{a1})_r S(O)_p R^{a3}$, —$(CR^aR^{a1})_r SO_2 NR^aR^{a1}$, —$(CR^aR^{a1})_r NR^a SO_2 R^{a3}$, $C_{1-6}$ alkyl, $C_{2-6}$ alkenyl, $C_{2-6}$ alkynyl, $C_{3-6}$ cycloalkyl substituted with 0–1 $R^{c1}$, phenyl substituted with 0–2 $R^{c1}$, or 5–6 membered heterocycle consisting of carbon atoms and 1–4 heteroatoms selected from N, O, and $S(O)_p$, and substituted with 0–2 $R^{c1}$;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of: carbon atoms and 0–2 heteroatoms selected from N, O, and $S(O)_p$;

each $R^d$ is, independently at each occurrence, $C_{1-6}$ alkyl, $OR^a$, Cl, F, Br, =O, $NR^aR^{a1}$, $C(O)R^a$, $C(O)OR^a$, $C(O)NR^aR^{a1}$, $S(O)_2NR^aR^{a1}$, $NR^aS(O)_2R^{a3}$, $S(O)_pR^{a3}$, $CF_3$ or phenyl;

r, at each occurrence, is selected from 0, 1, 2, and 3;
s, at each occurrence, is selected from 0, 1, 2, and 3; and
t, at each occurrence, is selected from 0, 1, 2, and 3.

In a fourth aspect, the present invention includes compounds of Formula (II):

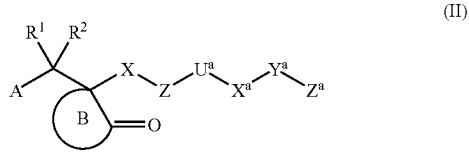

(II)

or a stereoisomer or pharmaceutically acceptable salt or solvate form thereof, wherein;

A is —C(O)NHOH;

X is absent, or is methylene;

ring B is substituted with 0–2 $R^3$ and is a 5–6 membered ring consisting of carbon atoms, 0–2 heteroatoms selected from N, O, and $S(O)_p$, 0–1 additional carbonyl groups, and 0–1 double bonds;

Z is a $C_{4-8}$ cycloalkyl substituted with 0–3 $R^b$, a $C_{4-8}$ cycloalkenyl substituted with 0–3 $R^b$, phenyl substituted with 0–4 $R^b$, naphthyl substituted with 0–5 $R^b$, or a heterocycle substituted with 0–3 $R^b$ and selected from furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, isoquinolinyl, methylenedioxyphenyl, and quinazolinyl;

$Z^a$ is phenyl substituted with 0–3 $R^c$, naphthyl substituted with 0–3 $R^c$, or a heterocycle substituted with 0–3 $R^c$ and selected from furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolo[1,5-a]pyridinyl;

each Q is, independently at each occurrence, H, a $C_{3-10}$ carbocycle substituted with 0–5 $R^d$, or a 5–10 membered heterocycle consisting of carbon atoms and 1–4 heteroatoms selected from N, O, and $S(O)_p$, and substituted with 0–3 $R^d$;

each $R^{a1}$ is, independently at each occurrence, H, $C_{1-6}$ alkyl, phenyl, or benzyl;

each $R^{a3}$ is, independently at each occurrence, H, $C_{1-6}$ alkyl, phenyl, or benzyl;

each $R^c$ is, independently at each occurrence, H, $OR^a$, Cl, F, Br, =O, $CF_3$, $CH_2F$, $CHF_2$, —$(CR^aR^{a1})_rNR^aR^{a1}$, —$(CR^aR^{a1})_rC(O)R^{a1}$, —$(CR^aR^{a1})_rC(O)OR^{a1}$, —$(CR^aR^{a1})_r$ C(O)$NR^aR^{a1}$, —$(CR^aR^{a1})_rNR^aC(O)R^{a1}$, —$(CR^aR^{a1})_sS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl, $C_{2-6}$ alkenyl, $C_{2-6}$ alkynyl, phenyl substituted with 0–2 $R^{c1}$, or 5–6 membered heterocycle consisting of carbon atoms and 1–4 heteroatoms selected from N, O, and $S(O)_p$, and substituted with 0–2 $R^{c1}$; and, alternatively, when two $R^c$ groups are attached to adjacent carbon atoms, together with the carbon atoms to which they are attached they form a 5–6 membered carbocyclic or heterocyclic ring D substituted with 0–2 $R^{c1}$ and consisting of: carbon atoms and 0–2 heteroatoms selected from N, O, and $S(O)_p$.

In a fifth aspect, the present invention includes compounds of Formula (II) or a stereoisomer or pharmaceutically acceptable salt or solvate form thereof, wherein:

Z is phenyl substituted with 0–4 $R^b$, thienyl substituted with 0–2 $R^b$, thiazolyl substituted with 0–1 $R^b$, oxazolyl substituted with 0–1 $R^b$, isoxazolyl substituted with 0–1 $R^b$, or imidazolyl substituted with 0–1 $R^b$;

$U^a$ is absent or is O;

$X^a$ is absent or is $C_{1-4}$ alkylene, $C_{2-4}$ alkenylene, or $C_{2-4}$ alkynylene;

$Y^a$ is absent or is O;

$R^2$ is $Q^1$, —$C_{1-6}$ alkylene-$Q^1$, —$C_{2-6}$ alkenylene-$Q^1$, —$C_{2-6}$ alkynylene-$Q^1$, —$(CH_2)_rO(CH_2)_s$-$Q^1$, —$(CH_2)_rNR^a(CH_2)_s$-$Q^1$, —$(CH_2)_rC(O)(CH_2)_s$-$Q^1$, —$(CH_2)_rC(O)O(CH_2)_s$-$Q^1$, —$(CH_2)_rC(O)NR^a(CH_2)_s$-$Q^1$, —$(CH_2)_rNR^aC(O)(CH_2)_s$-$Q^1$, —$(CH_2)_rS(O)_p(CH_2)_s$-$Q^1$, —$(CH_2)_rSO_2NR^a(CH_2)_s$-$Q^1$, or —$(CH_2)_rNR^aSO_2(CH_2)_s$-$Q^1$;

$R^3$ is H, $C_{1-4}$ alkyl, $C_{2-4}$ alkenyl, $C_{2-4}$ alkynyl, phenyl, or benzyl;

each Q is, independently at each occurrence, H, a $C_{3-6}$ carbocycle or a 5–6 membered heterocycle consisting of carbon atoms and 1–4 heteroatoms selected from N, O, and $S(O)_p$;

each $R^a$ is, independently at each occurrence, H or $C_{1-4}$ alkyl;

each $R^{a1}$ is, independently at each occurrence, H or $C_{1-4}$ alkyl;

each $R^{a3}$ is, independently at each occurrence, H, $C_{1-4}$ alkyl, phenyl, or benzyl;

each $R^c$ is, independently at each occurrence, $C_{1-6}$ alkyl, $C_{2-6}$ alkenyl, $C_{2-6}$ alkynyl, $OR^a$, Cl, F, Br, =O, $CF_3$, $CH_2F$, $CHF_2$, —$NR^aR^{a1}$, —$(CR^aR^{a1})_rC(O)R^{a1}$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_sS(O)_pR^{a3}$, —$(CR^aR^{a1})_rSO_2NR^aR^{a1}$, —$(CR^aR^{a1})_rNR^aSO_2R^{a3}$, or phenyl; and alternatively, when two $R^c$ groups are attached to adjacent carbon atoms, together with the carbon atoms to which they are attached they form a 5–6 membered carbocyclic or heterocyclic ring D substituted with 0–1 $R^{c1}$ and consisting of: carbon atoms and 0–2 heteroatoms selected from N, O, and $S(O)_p$.

In a sixth aspect, the present invention includes compounds of Formula (III):

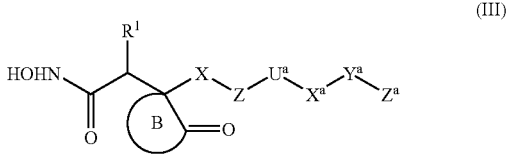

(III)

or a stereoisomer or pharmaceutically acceptable salt or solvate form thereof, wherein;

X is absent, or is methylene;

$R^1$ is H or $C_{1-6}$ alkylene;

each $Q^1$ is, independently at each occurrence, H, $C_{3-6}$ cycloalkyl substituted with 0–1 $R^d$, phenyl substituted with 0–2 $R^d$, or a 5–6 membered heterocycle consisting of carbon atoms and 1–4 heteroatoms selected from N, O, and $S(O)_p$, and substituted with 0–2 $R^d$;

m, at each occurrence, is selected from 0, 1, and 2;

r, at each occurrence, is selected from 0, 1, and 2; and s, at each occurrence, is selected from 0, 1, and 2.

In a seventh aspect, the present invention includes compounds of Formula (III), wherein:

Z is phenyl substituted with 0–1 $R^b$;

$Z^a$ is phenyl substituted with 0–3 $R^c$, naphthyl substituted with 0–3 $R^c$, or a heterocycle substituted with 0–3 $R^c$ and selected from pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, pyrazolyl, and pyrazolo[1,5-a]pyridinyl;

provided that Z, $U^a$, $Y^a$, and $Z^a$ form other than a biphenyl group;

each $R^b$ is, independently at each occurrence, $C_{1-6}$ alkyl, $OR^a$, Cl, F, Br, —$NR^aR^{a1}$, —$C(O)R^a$, —$C(O)OR^a$, —$C(O)NR^aR^{a1}$, —$S(O)_2NR^aR^{a1}$, —$NR^aS(O)_2R^{a3}$, —$S(O)_pR^{a3}$, or $CF_3$;

each $R^c$ is, independently at each occurrence, $C_{1-6}$ alkyl, $C_{2-6}$ alkenyl, $C_{2-6}$ alkynyl, $OR^a$, Cl, F, Br, =O, —$NR^aR^{a1}$, $CF_3$, —$(CR^aR^{a1})_rC(O)R^{a1}$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)_pR^{a3}$, —$(CR^aR^{a1})_rSO_2NR^aR^{a1}$, or $(CR^aR^{a1})_rNR^aSO_2R^{a3}$; and alternatively, when two $R^c$ groups are attached to adjacent carbon atoms, together with the carbon atoms to which they are attached they form a 5–6 membered saturated ring consisting of: carbon atoms and 0–1 heteroatoms selected from N, O, and $S(O)_p$.

In a eighth aspect, the present invention provides a compound selected from Examples 1–5 or a stereoisomer or pharmaceutically acceptable salt or solvate form thereof.

In another embodiment, the present invention provides a novel process for making a compound of the present invention or a stereoisomer or pharmaceutically acceptable salt or solvate thereof.

In another embodiment, the present invention provides a novel intermediate for making a compound of the present invention or a stereoisomer or pharmaceutically acceptable salt or solvate thereof.

In another embodiment, the present invention provides a novel pharmaceutical composition, comprising: a pharmaceutically acceptable carrier and a therapeutically effective amount of a compound of the present invention or a pharmaceutically acceptable salt or solvate form thereof.

In another embodiment, the present invention provides a novel method for treating or preventing an inflammatory disorder, comprising: administering to a patient in need thereof a therapeutically effective amount of a compound of the present invention or a pharmaceutically acceptable salt or solvate form thereof.

In another embodiment, the present invention provides a novel method of treating a condition or disease mediated by MMPs, and/or TACE, or a combination thereof in a mammal, comprising: administering to the mammal in need of such treatment a therapeutically effective amount of a compound of the present invention or a pharmaceutically acceptable salt or solvate form thereof.

In another embodiment, the present invention provides a novel method comprising: administering a compound of the present invention or a pharmaceutically acceptable salt or solvate form thereof in an amount effective to treat a condition or disease mediated by MMPs, and/or TACE, or a combination thereof.

In another embodiment, the present invention provides a novel method of treating a disease or condition selected from acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

In another embodiment, the present invention provides novel compounds of the present invention for use in therapy.

In another embodiment, the present invention provides the use of novel compounds of the present invention for the manufacture of a medicament for the treatment of a condition or disease mediated by MMPs, and/or TACE, or a combination thereof.

In another embodiment, the present invention provides a method for treating inflammatory disorders, comprising: administering, to a host in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

In another embodiment, the present invention provides a novel article of manufacture, comprising:

(a) a first container;
(b) a pharmaceutical composition located within the first container, wherein the composition, comprises: a first therapeutic agent, comprising: a compound of the present invention or a pharmaceutically acceptable salt or solvate form thereof; and,
(c) a package insert stating that the pharmaceutical composition can be used for the treatment of an inflammatory disorder.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt or solvate form thereof; and,
(c) a package insert stating that the pharmaceutical composition can be used in combination with a second therapeutic agent to treat an inflammatory disorder.

In another preferred embodiment, the present invention provides a novel article of manufacture, further comprising:
(d) a second container;

wherein components (a) and (b) are located within the second container and component (c) is located within or outside of the second container.

This invention also encompasses all combinations of preferred aspects of the invention noted herein. It is understood that any and all embodiments of the present invention may be taken in conjunction with any other embodiment to describe additional even more preferred embodiments of the present invention. It is also understood that each and every element of any embodiment is intended to be a separate specific embodiment. Furthermore, any elements of an embodiment are meant to be combined with any and all other elements from any of the embodiments to describe additional embodiments.

Definitions

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Accordingly, the present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All tautomers of shown or described compounds are also considered to be part of the present invention.

Preferably, the molecular weight of compounds of the present invention is less than about 500, 550, 600, 650, 700, 750, 800, 850, or 900 grams per mole. More preferably, the molecular weight is less than about 850 grams per mole. Even more preferably, the molecular weight is less than about 750 grams per mole. Still more preferably, the molecular weight is less than about 700 grams per mole.

As used herein, the term "alkyl" or "alkylene" is intended to include both branched and straight-chain saturated aliphatic hydrocarbon groups having the specified number of carbon atoms. For example, "$C_1$–$C_{10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$–$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_2$–$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_2$–$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo. "Haloalkyl" refers to branched and straight-chained, having one or more halogen substituents. Example haloalkyl groups include, but are not limited to, $CF_3$, $C_2F_5$, $CHF_2$, $CCl_3$, $CHCl_2$, $C_2C_5$, and the like.

The term "alkoxy" or "alkyloxy" refers to an —O-alkyl group. "$C_1$–$C_6$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy, and the like. Similarly, "alkylthio" or "thioalkoxy" represents an alkyl group as defined above with the indicated number of carbon atoms attached through a sulphur bridge; for example methyl-S—, ethyl-S—, and the like.

"Haloalkoxy" or "haloalkyloxy" represents a haloalkyl group as defined above with the indicated number of carbon atoms attached through an oxygen bridge. For example, "$C_1$–$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, phenanthranyl, and the like. Aryl moieties are well known and described, for example, in *Hawley's Condensed Chemical Dictionary* (13 ed.), R. J. Lewis, ed., J. Wiley & Sons, Inc., New York (1997). Aryl groups can be substituted or unsubstituted.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, acridinyl, azocinyl, benzimidazolyl, benzofuranyl, benzothiophenyl, benzoxazolyl, benzthiazolyl, benztriazolyl, benzisoxazolyl, benzisothiazolyl, benzimidazolinyl, carbazolyl, 4H-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thienyl, triazinyl, 1,2,3-triazolyl, 1,2,4-triazolyl, 1,2,5-triazolyl, 1,3,4-triazolyl, xanthenyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, imidazo[1,2-a]pyridinyl, imidazo[1,5-a]pyridinyl, and pyrazolo[1,5-a]pyridinyl. Also included are fused ring and spiro compounds containing, for example, the above heterocycles.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a small, negatively charged species such as chloride, bromide, hydroxide, acetate, and sulfate.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

When any variable (e.g., $R^{2a}$, $R^{2b}$, etc.) occurs more than one time in any constituent or formula for a compound, its definition at each occurrence is independent of its definition at every other occurrence. Thus, for example, if a group is shown to be substituted with 0–3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations result in stable compounds.

The term "independently selected from", "independently at each occurrence" or similar language, means that the labeled R substitution group may appear more than once and that each appearance may be a different atom or molecule found in the definition of that labeled R substitution group. Thus if the labeled $R^a$ substitution group appear four times in a given permutation of Formula I, then each of those labeled $R^a$ substitution groups may be a different group falling in the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are amines on the compounds of this invention, these can be converted to amine N-oxides by treatment with MCPBA and or hydrogen peroxides to afford other compounds of this invention. Thus, all shown amines are considered to cover both the shown amine and its N-oxide (N→O) derivative.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to acid or base salts of the compounds described herein. Examples of pharmaceutically acceptable salts include, but are not limited to, mineral or organic acid salts of basic residues such as amines; alkali or organic salts of acidic residues such as carboxylic acids; and the like. Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference in its entirety. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Prodrugs" refer to inactive compounds that can be converted upon absorption by a mammalian subject to an active compound of the present invention. Prodrugs of the compounds of the present invention can be prepared by modifying functional groups present in the compounds of the present invention in such a way that the modifications are cleaved in vivo to produce the parent compounds. Examples of prodrugs include, but are not limited to, acetate, formate and benzoate derivatives of alcohol and amine functional groups in the compounds of the present invention. Preparation of prodrugs is well known in the art and described in, for example, *Medicinal Chemistry: Principles and Practice*, ed. F. D. King, The Royal Society of Chemistry, Cambridge, UK, 1994, which is incorporated herein by reference in its entirety.

Radiolabelled compounds of the present invention, i.e., wherein one or more of the atoms described are replaced by a radioactive isotope of that atom (e.g., C replaced by $^{13}C$ or by $^{14}C$; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor XIa. "Therapeutically effective amount" is also intended to include an amount of the combination of compounds claimed that is effective to inhibit factor XIa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, which is incorporated herein by reference in its entirety.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1999).

All references cited herein are hereby incorporated in their entirety herein by reference.

A variety of compounds of formula (I), wherein A is a hydroxamic acid group, can be prepared from their corresponding esters via several routes known in the literature (Scheme 1). The methyl ester of 1 ($R^{11}$=Me) can be directly converted to hydroxamic acid 2 by treatment with hydroxylamine under basic conditions such as KOH or NaOMe in solvents such as methanol. The methyl ester of 1 ($R^{11}$=Me) can also be converted to O-benzyl protected hydroxamic acid with O-benzylhydroxylamine under similar conditions or using Weinreb's trimethylalluminum conditions (Levin, J. I.; Turos, E.; Weinreb, S. M. *Syn. Commun.* 1982, 12, 989) or Roskamp's bis[bis(trimethylsilyl)amido]tin reagent (Wang, W.-B.; Roskamp, E. J. *J. Org. Chem.* 1992, 57, 6101). The benzyl ether is removed by methods well known in the literature (e.g., hydrogenation using palladium on barium sulfate) to give compound 2. Alternatively, 2 can be prepared through carboxylic intermediate 3. Carboxylic acid 3 can be converted to 2 via coupling with hydroxylamine or O-benzylhydroxylamine followed by deprotection.

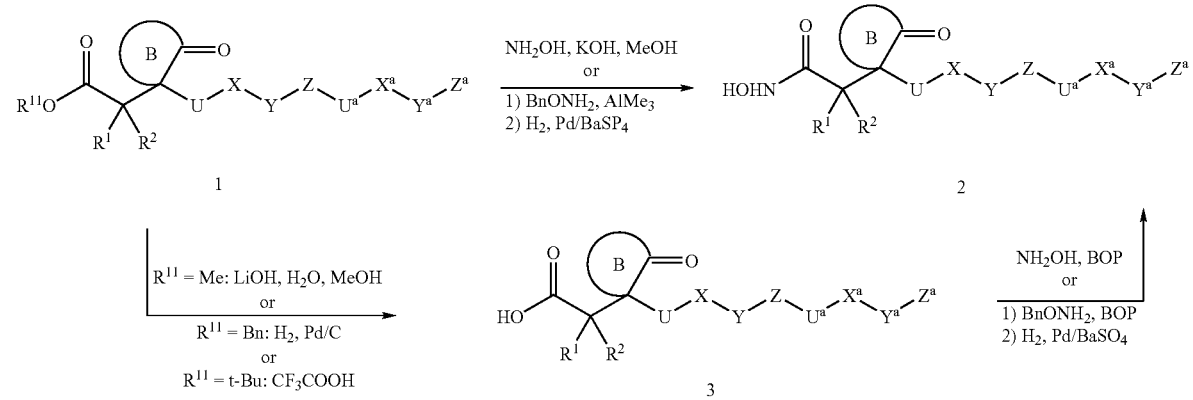

Scheme 1

The preparation of esters such as 1 can be accomplished following procedures found in the literature. One such way is described in Scheme 2. Ketone 4 can be alkylated with a bromoacetic acid ester using a lithium amide as a base to provide ester 5 (see for example: Mazzocchi, P. H.; Kim, C. H. *J. Heterocycl. Chem.* 1985, 22, 677–680). Substitution adjacent to the ester functional group can then be carried out utilizing enolate alkylation chemistry subsequent to protection of the ring carbonyl. Final deprotection of the ring ketone should give the desired ester 1.

Scheme 2

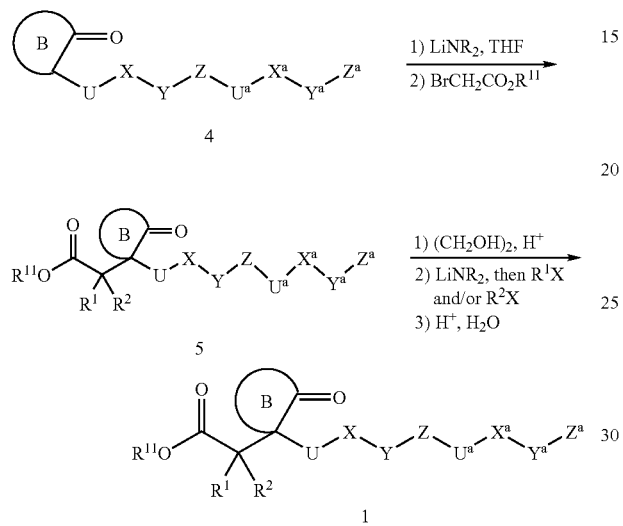

An alternative approach for the construction of ester 1 takes advantage of the well-documented nature of β-ketoesters such as 6 to undergo aldol additions, Michael additions, alkylations, etc. (see Scheme 3). For instance, ketoester 6 can be subjected to an aldol addition or alkylation with subunit 7 to give coupled product 8. The presence of a compatible functionality in subunit 7 will dictate which type of reaction is performed and consequently the exact structure of product 8. After protection of the ketone as a cyclic ketal, the ester of 8 can be reduced, and the resultant alcohol can be converted into a triflate to provide 9. Displacement of the triflate with sodium cyanide followed by hydrolysis of the nitrite with concomitant removal of the ketal protecting group should give the homologated ester 5.

Scheme 3

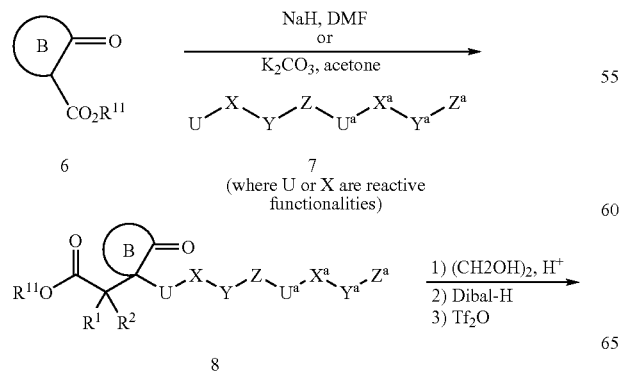

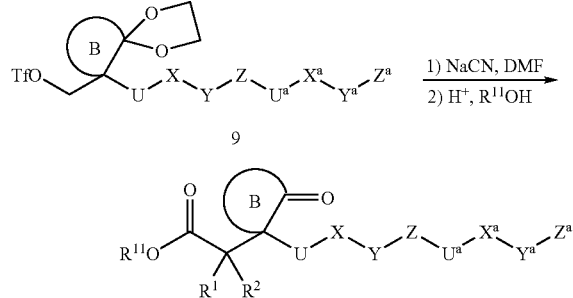

A versatile route for the preparation of inhibitors wherein ring B is a lactam is outlined in Scheme 4. Lactam 10 can be alkylated with LDA and benzyl chloride 11 to give substituted lactam 12. A second alkylation with t-butyl bromoacetate utilizing the same conditions as the first should provide 13. After hydrogenation of the benzyl-protecting group using Pearlman's catalyst, the resultant phenol 14 can be alkylated with halide 15 to give ester 16. Ester 16 can be converted into the corresponding hydroxamic acid via the routes exemplified in Scheme 1.

Scheme 4

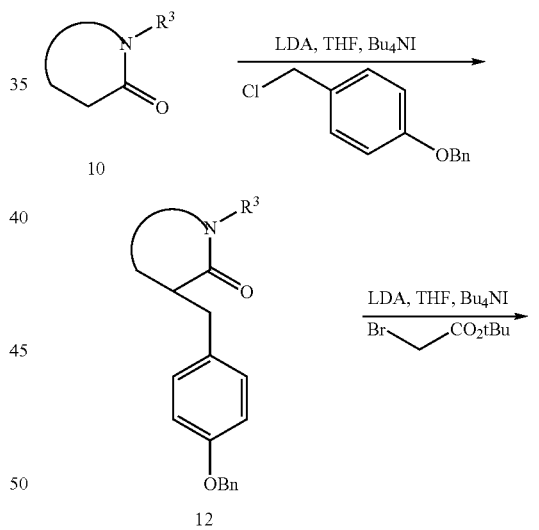

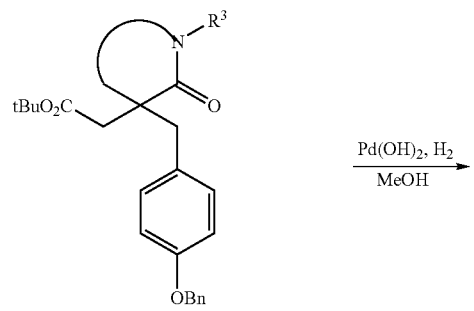

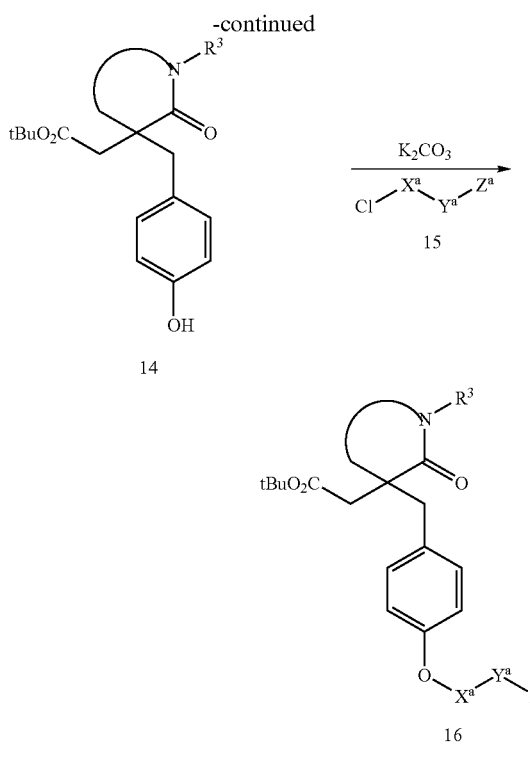

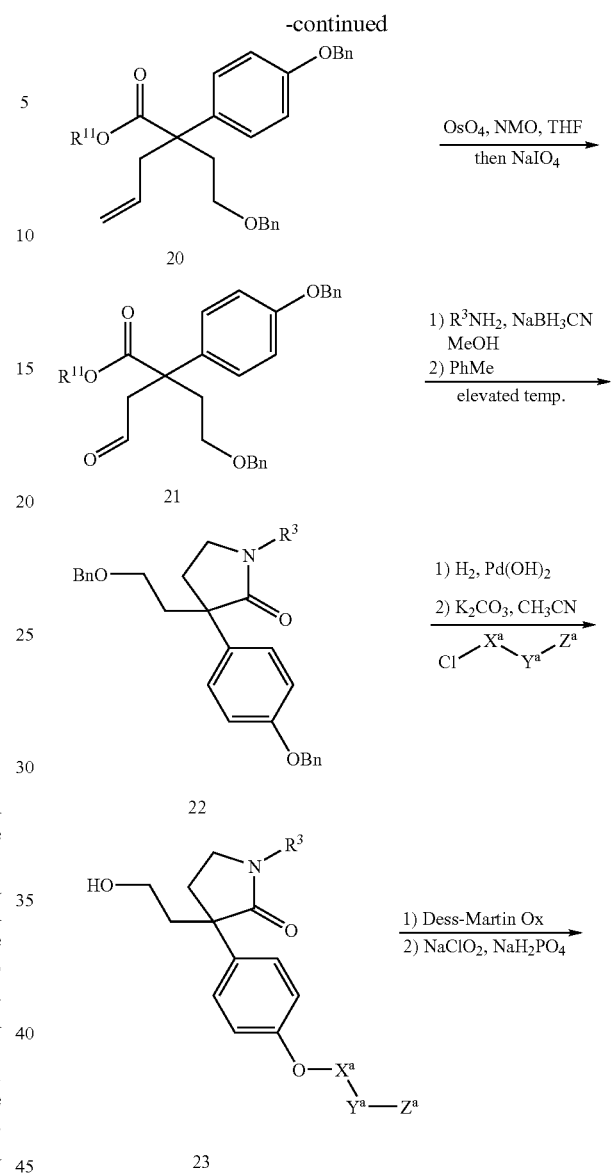

Another method for the preparation of inhibitors wherein ring B is a lactam is shown in Scheme 5. The lithium enolate of ester 17 can be alkylated with iodide 18 to give ester 19. Subsequent alkylation of 19 with allyl bromide should provide the bis-alkylated product 20. Oxidation of the olefin of 20 with osmium tetroxide followed by cleavage of the resultant diol with sodium periodate should give rise to aldehyde 21. Reductive amination of aldehyde 21 with a primary amine and subsequent cyclization should furnish lactam 22. After removal of both benzyl-protecting groups, the phenol can be alkylated with halide 15 to give alcohol 23. Oxidation of alcohol 23 to carboxylic acid 24 can be accomplished via a two-step oxidation sequence. Acid 24 can be converted into the corresponding hydroxamic acid according to the methods outlined in Scheme 1.

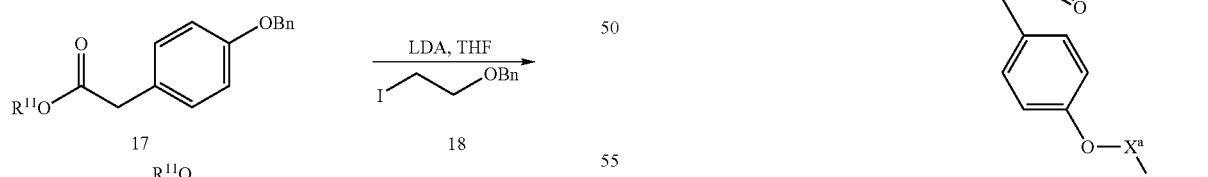

A useful method for the preparation of compounds wherein ring B is a dihydro-pyridazin-3-one is depicted in Scheme 6. Ester 21, prepared as shown in Scheme 5, can be condensed with hydrazine in refluxing THF to give the annulated product 25. A four-step sequence similar to that shown in Scheme 5 involving removal of the benzyl ethers, alkylation of the phenol with halide 15, and a 2-step oxidation should result in the conversion of 25 into carboxylic acid 27. Acid 27 can be converted into the corresponding hydroxamic acid according to the methods outlined in Scheme 1.

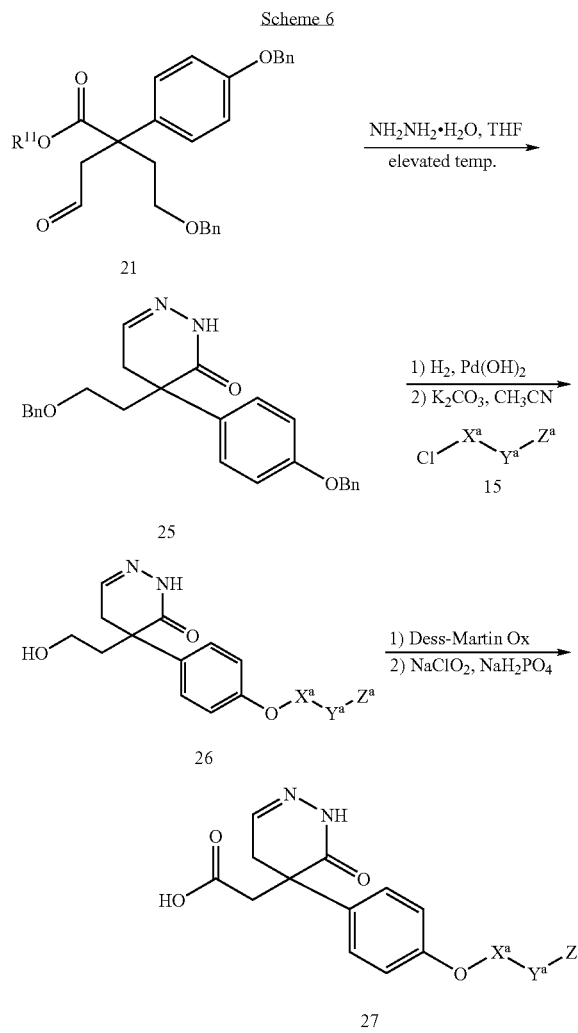

One stereoisomer of a compound of Formula I may display superior activity compared with the others. Thus, the following stereochemistries are considered to be a part of the present invention.

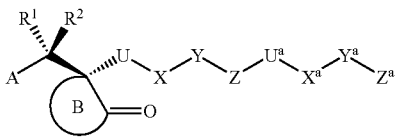

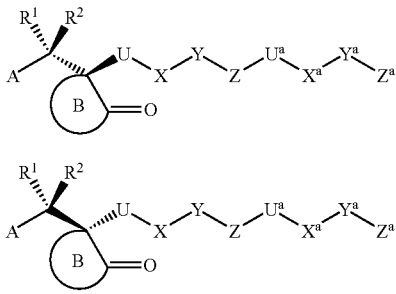

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "µg" for microgram, "mL" for milliliter or milliliters, "µL" for microliter(s), "mmol" for millimolar, "M" for molar, "mM" denotes millimolar, "nM" denotes nanomolar, "µM" denotes micromolar, "nm" for nanometer, "meq" for milliequivalent(s), "min" for minute or minute(s), "atm" for atmosphere, "conc." for concentrated, "MW" for molecular weight, "mp" for melting point, "rt" or "RT" for room temperature, "sat" or "sat'd" for saturated "$^1$H" for proton, "MHz" for megahertz, "MS" for mass spectroscopy, "NMR" for nuclear magnetic resonance spectroscopy, "rt" for room temperature, "tlc" for thin layer chromatography, "v/v" for volume to volume ratio, "ESI" for electrospray ionization mass spectroscopy, "HPLC" for high performance liquid chromatography, "MS" for mass spectrometry, "LC/MS" for liquid chromatography mass spectrometry, "NMR" for nuclear magnetic resonance spectroscopy, and "TLC" for thin layer chromatography. "Sigma" stands for the Sigma-Aldrich Corp. of St. Louis, Mo.

Solution ratio expresses a volume relationship, unless stated otherwise. NMR chemical shifts (δ) are reported in parts per million. Flash chromatography was carried out on silica gel according to Still's method (Still, W. C. et al. *J. Org. Chem.* 1978,43, 2923).

As used throughout the specification, the following abbreviations for chemical reagents apply:
HOAc or AcOH=acetic acid
Bn=benzyl
Bu=butyl
t-Bu=tertiary butyl
Boc=tert-butyl oxycarbonyl
DMF=dimethylformamide
DMSO=dimethyl sulfoxide
Et=ethyl
EtOH=ethanol
EtOAc=ethyl acetate
Me=methyl
MeOH=methanol
NaOAc=sodium actetate
OAc=acetate
Ph=phenyl
Pr=propyl
i-Pr=isopropyl
i-PrOH=isopropanol TFA=trifluoroacetic acid THF=tetrahydrofuran "α", "β", "R", "S", "E", and "Z" are stereochemical designations familiar to one skilled in the art. One stereoisomer of a compound of Formula (I) may display superior activity compared with the others. Thus, each stereoisomer of a compound of Formula (I) is considered to be a part of the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of Formula (I) may also be directly synthesized using a chiral catalyst or a chiral ligand, e.g., Jacobsen, E. *Acc. Chem. Res.* 2000, 33, 421–431 or using other enantio- and diastereo-selective reactions and reagents known to one skilled in the art of asymmetric synthesis.

Other features of the invention will become apparent in the course of the following descriptions of exemplary embodiments that are given for illustration of the invention and are not intended to be limiting thereof.

Example 1

N-hydroxy-2-(1-methyl-3-{4-[(2-methyl-4-quinolinyl)methoxy]benzyl}-2-oxo-3-piperidinyl)acetamide (1a)

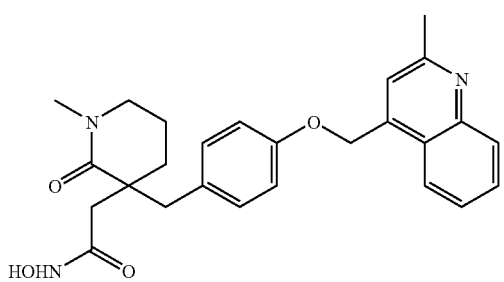

To a solution of diisopropylamine (1.03 g, 10.2 mmol) in THF at −78° C. was added n-butyllithium (6.36 mL of a 1.6 M solution, 10.2 mmol). After stirring for 10 min, a solution of 1-methyl-2-piperidone (1.05 g, 9.3 mmol) in THF was added dropwise. The mixture was allowed to stir for 30 min. A solution of 4-benzyloxybenzyl chloride (2.15 g, 9.3 mmol) in THF was added followed by the addition of a catalytic amount of tetrabutylammonium iodide (684 mg). The mixture as stirred at −78° C. for 10 min, then allowed to gradually warm to rt overnight. The reaction was quenched with saturated ammonium chloride and diluted with ethyl acetate. The layers were separated and the organic layer washed with brine, dried over magnesium sulfate, filtered, and concentrated. Purification of the crude material by silica gel chromatography (25% ethyl acetate/hexanes) provided the desired product (2.05 g, 72%). MS found: $(M+H)^+=310$.

(1b)

Following a procedure analogous to that used in reaction (1a), the piperidone (1.05 g, 3.39 mmol) from reaction (1a) was alkylated with t-butyl bromoacetate (1.3 g, 6.8 mmol). Purification of the crude material by silica gel chromatography (25% ethyl acetate/hexanes) provided the desired product (378 mg, 26%). MS found: $(M+H)^+=424$.

(1c)

To a solution of the benzyl ether (378 mg, 0.89 mmol) from reaction (1b) in methanol was added palladium hydroxide on carbon (76 mg). The mixture was exposed to an atmosphere of hydrogen for 48 h, filtered, and concentrated to give the desired phenol (284 mg, 96%), which was used in subsequent steps without further purification. MS found: $(M+H)^+=334$.

(1d)

A solution of the phenol (284 mg, 0.85 mmol) from reaction (1c), potassium carbonate (270 mg, 2.0 mmol), sodium iodide (7 mg), and 2-methyl-4-chloromethylquinoline (256 mg, 1.3 mmol) in acetonitrile was heated at reflux overnight. The mixture was concentrated and partitioned between ethyl acetate and water. The layers were separated and the organic layer washed with additional water and brine, dried, and concentrated. Purification of the crude material by silica gel chromatography (50% ethyl acetate/hexanes) provided the desired material (376 mg, 86%). MS found: $(M+H)^+=489$.

(1e)

To a solution of the t-butyl ester (376 mg, 0.77 mmol) from reaction (1d) in methanol was bubbled hydrogen chloride (gas) for 15 min. The mixture was allowed to stir at rt overnight. After the solvent was removed in vacuo, the residue was diluted with ethyl acetate and washed with 1 N sodium hydroxide solution (2×), dried, and concentrated to give the methyl ester (310 mg, 90%). This material was used without further purification. MS found: $(M+H)^+=447$.

(1f)

Preparation of hydroxylamine/sodium methoxide solution: sodium methoxide (11.9 mL, 51.8 mmol), as a 25 w/w % solution in methanol, was added to a hot solution of hydroxylamine hydrochloride (2.40 g, 34.5 mmol) in methanol (9 mL). After the mixture cooled to rt, the precipitate was removed by filtration. The filtrate was used fresh and was assumed to have a hydroxylamine concentration of 1.64 M. The hydroxylamine solution (6.84 mL of a 1.64 M solution, 11.6 mmol) was added to the methyl ester (173 mg, 0.39 mmol) from reaction (1e). After stirring for 30 min at rt, the reaction was acidified to pH 7 with concentrated HCl. The mixture was filtered to remove the precipitated salts, and the resulting material purified by reverse phase HPLC (10–40% acetonitrile/water) to provide the hydroxamic acid (87 mg, 40%). MS found: $(M+H)^+=448$.

Example 2

N-hydroxy-2-(1-methyl-3-{4-[(2-methyl-4-quinolinyl)methoxy]benzyl}-2-oxo-3-pyrrolidinyl)acetamide (2a)

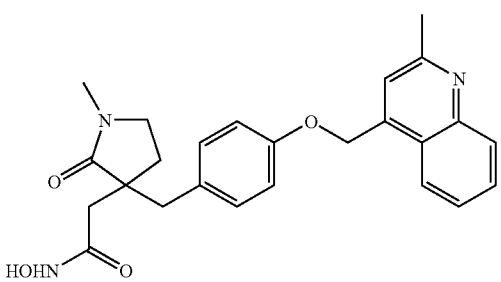

Following a procedure analogous to that used in reaction (1a), 1-methyl-2-pyrrolidinone (1.15 g, 11.6 mmol) was alkylated with 4-benzyloxybenzyl chloride (2.78 g, 11.6 mmol). Purification of the crude material by silica gel chromatography (2% methanol/methylene chloride) gave the desired product (2.56 g, 75%). MS found: (M+H)⁺=296.

(2b)
Following a procedure analogous to that used in reaction (1a), the pyrrolidinone (1.05 g, 3.55 mmol) from reaction (2a) was alkylated with t-butyl bromoacetate (1.38 g, 7.1 mmol). Purification of the crude material by silica gel chromatography (methylene chloride-2% methanol/methylene chloride) provided the desired product (302 mg, 21%). MS found: (M+H)⁺=410.

(2c)
Following a procedure analogous to that used in reaction (1c), the benzyl ether (302 mg, 0.74 mmol) from reaction (2b) was hydrogenated to give the desired phenol (206 mg, 89%) and was used in the subsequent step without further purification. MS found: (M+H)⁺=320.

(2d)
Following a procedure analogous to that used in reaction (1d), the phenol (206 mg, 0.64 mmol) from reaction (2c) was reacted with 2-methyl-4-chloromethylquinoline (185 mg, 0.97 mmol). Purification of the crude material by silica gel chromatography (2% methanol/methylene chloride) gave the desired product (136 mg, 44%). MS found: (M+H)⁺=475.

(2e)
Following a procedure analogous to that used in reaction (1e), the t-butyl ester (136 mg, 0.29 mmol) from reaction (2d) was reacted with hydrogen chloride (g) to give the desired methyl ester (124 mg, 100%). MS found: (M+H)⁺=433.

(2f)
Following a procedure analogous to that used in reaction (1f), the methyl ester (124 mg, 0.29 mmol) from reaction (2e) was reacted with hydroxylarmine. Purification of the crude material by reverse phase HPLC (10–40% acetonitrile/water) provided the desired hydroxamic acid (30 mg, 19%). MS found: (M+H)⁺=434.

Example 3

N-hydroxy-2-(1-methyl-3-{4-[(2-methyl-4-quinolinyl)methoxy]phenyl}-2-oxo-3-pyrrolidinyl)acetamide (3a)

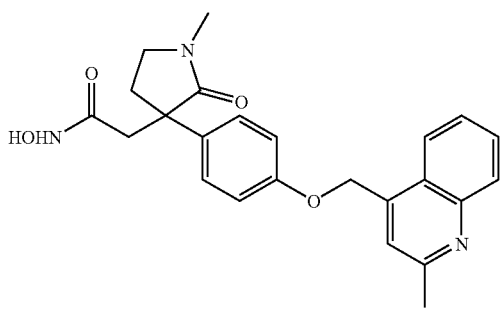

To a solution of 2-(benzyloxy)ethanol (75.0 g, 493 mmol), triphenylphosphine (142.1 g, 542 mmol), and imidazole (36.9 g, 542 mmol) in methylene chloride (1.5 L) at 0° C. was added iodine (143.9 g, 567 mmol). The mixture was stirred at 0° C. for 2 h. The solvent was removed in vacuo and the remaining residue was filtered through a pad of silica gel eluting with 10% ethyl acetate/hexanes. The filtrate was then washed with a 1:1 solution of 10% sodium sulfite/saturated sodium bicarbonate (2×), saturated sodium bicarbonate (1×), and brine. The organic layer was dried and concentrated to give the desired iodide (123.6 g, 96%), which was used without further purification or characterization.

(3b)
To a solution of methyl 4-benzyloxyphenylacetate (75.0 g, 293 mmol) in THF (800 mL) at −78° C. was added sodium bis(trimethylsilyl)amide (322 mL of a 1 M solution in THF, 322 mmol) over 30 min. After stirring for 1 h, 1,3-dimethyl-3,4,5,6-tetrahydro-2(1H)-pyrimidinone (DMPU) (88.5 mL, 731.5 mmol) was added followed by the addition of a solution of the iodide (84.4 g, 322 mmol) from reaction (3a) in THF. The mixture was allowed to warm to 0° C. and stir for 2 h. The reaction was quenched with saturated ammonium chloride (500 mL), and the volatiles were removed under reduced pressure. The remaining residue was diluted with water and a solution of hexanes/diethyl ether (2:1). The layers were separated and the water layer back-extracted with hexanes/diethyl ether (2:1). The combined organic layers were washed with brine, dried, and concentrated. The remaining residue was filtered through a pad of silica gel eluting with 20% ethyl acetate/hexanes and concentrated to give the desired product (100%).

(3c)
Following a procedure analogous to that used in reaction (3b), the ester (114.3 g, 293 mmol) from reaction (3b) was alkylated with allyl bromide (38.0 mL, 439 mmol). The crude residue was filtered through a pad of silica gel eluting with 20% ethyl acetate/hexanes to provide the desired product (100 g, 80%). MS found: (M+H)⁺=431.

(3d)
To a solution of the ester (2.78 g, 6.45 mmol) from reaction (3c) in THF/water (3:1) was added osmium tetraoxide (8.2 mL of a 1 g/100 mL solution in water, 0.32 mmol) and N-methylmorpholine N-oxide (906 mg, 7.74 mmol). After stirring for 3 h, sodium periodate (2.07 g, 9.7 mmol) was added and the mixture was allowed to stir for 90 min. The mixture was partitioned between ethyl acetate and water. The organic layer was washed with 10% sodium sulfite solution (2×), dried, and concentrated. Purification of the crude material by silica gel chromatography (25% ethyl acetate/hexanes) provided the desired aldehyde (2.07 g, 74%). MS found: (M+H)⁺=433.

(3e)
To a solution of the aldehyde (62 mg, 0.14 mmol) from reaction (3d), methylamine (1.86 mL, 3.7 mmol), and methylamine hydrochloride (39 mg, 0.57 mmol) in methanol was added sodium cyanoborohydride (12 mg, 0.19 mmol). The mixture was allowed to stir overnight and concentrated. The remaining residue was dissolved in toluene and heated at reflux overnight. The solution was again concentrated and the crude residue purified by silica gel chromatography to give the desired lactam (35 mg, 59%). MS found: (M+H)⁺=416.

(3f)
Following a procedure analogous to that used in reaction (1c), the benzyl ether (190 mg, 0.46 mmol) from reaction (3e) was hydrogenated to give the desired alcohol/phenol (108 mg, 100%). MS found: (M+H)⁺=236.

(3g)
Following a procedure analogous to that used in reaction (1d), the phenol (108 mg, 0.46 mmol) from reaction (3f) was reacted with 2-methyl-4-chloromethylquinoline (96 mg, 0.50 mmol). Purification of the crude material by silica gel chromatography (2% methanol/methylene chloride) provided the desired product (142 mg, 80%). MS found: $(M+H)^+=391$.

(3h)

To a solution of the alcohol (142 mg, 0.36 mmol) from reaction (3g) in methylene chloride was added the Dess-Martin periodinane reagent (154 mg, 0.36 mmol). The mixture immediately turned cloudy. The solution was made basic by the addition of 10% potassium carbonate solution. The layers were separated and the organic layer dried and concentrated to give the desired aldehyde (140 mg, 99%), which was used in the subsequent step without further purification. MS found: $(M+H)^+=389$.

(3i)

To a solution of the aldehyde (140 mg, 0.36 mmol) from reaction (3h) and 2-methyl-2-butene (11 mL) in t-butanol (11 mL) and water (11 mL) at 0° C. was added sodium chlorite (201 mg, 80% pure, 1.77 mmol) followed by sodium dihydrogenphosphate (292 mg, 2.1 mmol). The mixture was allowed to warm to rt and stir for 3 h. The solution was adjusted to pH 4 and extracted with ethyl acetate (3×). The combined organic layers were dried and concentrated to give the desired carboxylic acid (139 mg, 96%). MS found: $(M+H)^+=405$.

(3j)

To a solution of the carboxylic acid (139 mg, 0.34 mmol) from reaction (3i), cesium carbonate (1.35 g, 4.1 mmol), and hydroxylamine hydrochloride (239 mg, 3.44 mmol) in DMF was added benzotriazol-1-yloxy-tris(dimethylamino)phosphonium hexafluorophosphate (228 mg, 0.52 mmol). The mixture was allowed to stir for 3 h. The mixture was concentrated and the crude residue purified by reverse phase HPLC (0–10–40% acetonitrile/water) to give the desired hydroxamic acid (40 mg, 22%). MS found: $(M+H)^+=420$.

Example 4

N-hydroxy-2-(1-(2-hydroxyethyl)-3-{4-[(2-methyl-4-quinolinyl)methoxy]phenyl}-2-oxo-3-pyrrolidinyl)acetamide (4a)

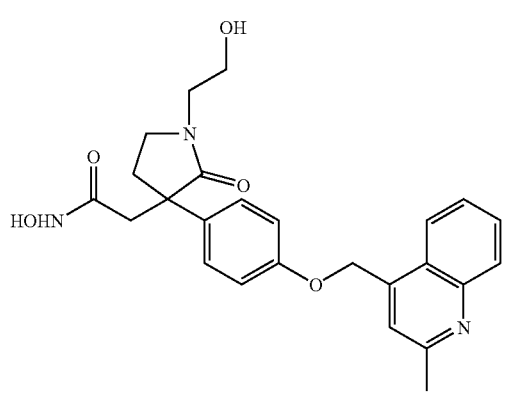

Following a procedure analogous to that used in reaction (3b), methyl 4-benzyloxyphenylacetate (10.0 g, 39.1 mmol) was alkylated with allyl bromide (4.73 g, 39.1 mmol). Purification of the crude material by silica gel chromatography (10% ethyl acetate/hexanes) provided the desired product (7.74 g, 67%). MS found: $(M+H)^+=297$.

(4b)

Following a procedure analogous to that used in reaction (1b), the ester (4.05 g, 13.7 mmol) from reaction (4a) was alkylated with t-butyl bromoacetate (2.66 g, 13.7 mmol). Purification of the crude material by silica gel chromatography (5% ethyl acetate/hexanes) gave the desired product (3.1 g, 55%). MS found: $(M+H)^+=411$.

(4c)

To a solution of the olefin (1.52 g, 3.7 mmol) from reaction (4b) in methylene chloride at −78° C. was bubbled ozone until the solution color remained a pale blue (approx. 30 min). The reaction was purged of excess ozone by bubbling nitrogen through the solution for 30 min. Triphenylphosphine (1.07 g, 4.1 mmol) was added and the reaction was allowed to warm to rt and stirred overnight. The solvent was removed, and the crude residue was purified by silica gel chromatography (10% ethyl acetate/hexanes) to give the desired aldehyde (1.22 g, 80%). MS found: $(M+H)^+=413$.

(4d)

To a solution of the aldehyde (118 mg, 0.29 mmol) from reaction (4c) and ethanolamine (26 mg, 0.43 mmol) in 1,2-dichloroethane (2 mL) and acetic acid (2 mL) was added magnesium sulfate. The mixture was stirred at rt for 45 min and was filtered. To the filtrate was added sodium triacetoxyborohydride (91 mg, 0.43 mmol) and the mixture stirred overnight. The volatiles were removed under reduced pressure, and the crude residue was diluted with ethyl acetate and water. The organic layer was washed with 1 N sodium hydroxide and brine, dried, and concentrated. The crude material was dissolved in acetonitrile and ytterbium (III) triflate (9 mg) was added. The mixture was heated at reflux for 2 days. The solution was concentrated, and the crude material was purified by silica gel chromatography (10% methanol/methylene chloride) to provide the desired lactam (52 mg, 41%). MS found: $(M+H)^+=426$.

(4e)

Following a procedure analogous to that used in reaction (1c), the benzyl ether (52 mg, 0.12 mmol) from reaction (4d) was hydrogenated to provide the desired phenol (40 mg, 100%). MS found: $(M+H)^+=336$.

(4f)

Following a procedure analogous to that used in reaction (1d), the phenol (40 mg, 0.12 mmol) from reaction (4e) was reacted with 2-methyl-4-chloromethylquinoline (35 mg, 0.18 mmol). Purification of the crude material by silica gel chromatography (2% methanol/methylene chloride) gave the desired product (45 mg, 75%). MS found: $(M+H)^+=491$.

(4g)

Following a procedure analogous to that used in reaction (1e), the t-butyl ester (45 mg, 0.092 mmol) from reaction (4f) was reacted with hydrogen chloride (g) to provide the desired methyl ester (35 mg, 85%). MS found: $(M+H)^+=449$.

(4h)

Following a procedure analogous to that used in reaction (1f), the methyl ester (35 mg, 0.078 mmol) from reaction (4g) was reacted with hydroxylamine. Purification of the crude material by reverse phase HPLC (10–40% acetonitrile/water) gave the desired hydroxamic acid (25 mg, 57%). MS found: $(M+H)^+=450$.

Example 5

N-hydroxy-2-(4-{4-[(2-methyl-4-quinolinyl)methoxy]phenyl}-3-oxo-2,3,4,5-tetrahydro-4-pyridazinyl)acetamide

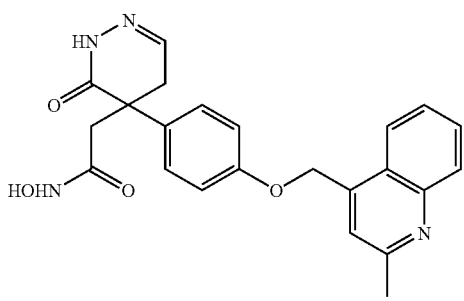

(5a)

A solution of the aldehyde (1.2 g, 2.78 mmol) from reaction (3d) and hydrazine hydrate (116 mg, 3.6 mmol) was heated at reflux for 3 days. The mixture was concentrated and the crude material purified by silica gel chromatography (25–33% ethyl acetate/hexanes) to give the desired product (1.05 g, 91%). MS found: $(M+H)^+=415$.

(5b)

To a solution of the benzyl ether (414 mg, 1.0 mmol) from reaction (5a) in methanol/ethyl acetate (1:1) was added palladium hydroxide on carbon (100 mg). The mixture was exposed to 50 psi of hydrogen for 3 days. The mixture was filtered and concentrated to give the desired phenol/alcohol (170 mg, 72%) and was used in the subsequent step without further purification. MS found: $(M+H)^+=334$.

(5c)

Following a procedure analogous to that used in reaction (1d), the phenol (170 mg, 0.72 mmol) from reaction (5b) was reacted with 2-methyl-4-chloromethylquinoline (165 mg, 0.86 mmol). Purification of the crude material by silica gel chromatography (100% ethyl acetate) provided the desired product (136 mg, 47%). MS found: $(M+H)^+=390$.

(5d)

Following a procedure analogous to that used in reaction (3h), the alcohol (136 mg, 0.35 mmol) from reaction (5c) was reacted with the Dess-Martin periodinane reagent (148 mg, 0.35 mmol) to give the desired aldehyde (132 mg, 98%). MS found: $(M+H)^+=388$.

(5e)

Following a procedure analogous to that used in reaction (3i), the aldehyde (132 mg, 0.34 mmol) from reaction (5d) was reacted with sodium chlorite to provide the desired carboxylic acid (120 mg, 88%). MS found: $(M+H)^+=404$.

(5f)

Following a procedure analogous to that used in reaction (1e), the carboxylic acid (120 mg, 0.3 mmol) from reaction (5e) was reacted with hydrogen chloride (g) to give the desired methyl ester (125 mg, 100%). MS found: $(M+H)^+=418$.

(5g)

Following a procedure analogous to that used in reaction (1f), the methyl ester (125 mg, 0.3 mmol) from reaction (5f) was reacted with hydroxylamine. Purification of the crude material by reverse phase HPLC (10–40% acetonitrile/water) provided the desired hydroxamic acid (6.5 mg, 4%). MS found: $(M+H)^+=419$.

Utility

The compounds of the present invention are expected to possess matrix metalloprotease and/or TNF-α inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of the present invention are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis (Stetler-Stevenson, *Cancer and Metastasis Reviews*, 1990, 9, 289–303). The compounds of the present invention should be useful for the prevention and treatment of invasive tumors by inhibition of this aspect of metastasis.

The compounds of the present invention should also have utility for the prevention and treatment of osteopenia associated with matrix metalloprotease-mediated breakdown of cartilage and bone that occurs in osteoporosis patients.

Compounds that inhibit the production or action of TACE and/or MMP's are potentially useful for the treatment or prophylaxis of various inflammatory, infectious, immunological or malignant diseases or conditions. Thus, the present invention relates to a method of treating various inflammatory, infectious, immunological or malignant diseases. These include acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia (including cachexia resulting from cancer or HIV), calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy (including inflammatory bowel disease), Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis (including juvenile rheumatoid arthritis and adult rheumatoid arthritis), sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

Some compounds of the present invention have been shown to inhibit TNF production in lipopolysacharride stimulated mice, for example, using the assay for TNF induction in mice and in human whole blood as described below.

The compounds of the present invention can be administered alone or in combination with one or more additional anti-inflammatory agents. These agents include, but are not limited to, selective COX-2 inhibitors,.interleukin-1 antagonists, dihydroorotate synthase inhibitors, p38 MAP kinase inhibitors, TNF-α inhibitors, and TNF-α sequestration agents.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term selective COX-2 inhibitors, as used herein, denotes agents that selectively inhibit COX-2 function. Such agents include, but are not limited to, celecoxib (Celebrex®), rofecoxib (Vioxx®), meloxicam (Movicox®), etoricoxib, and valdecoxib.

TNF-α sequestration agents that may be used in combination with the compounds of this invention, are TNF-α binding proteins or anti-TNF-α antibodies. These agents include, but are not limited to, etanercept (Enbrel®), infliximab (Remicade®), adalimumab (D2E7), CDP-571 (Humicade®), and CDP-870.

Other anti-inflammatory agents that may be used in combination with the compounds of this invention, include, but are not limited to, methotrexate, interleukin-1 antagonists (e.g., anakinra (Kineret®)), dihydroorotate synthase inhibitors (e.g., leflunomide (Arava®)), and p38 MAP kinase inhibitors.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

A compound is considered to be active if it has an $IC_{50}$ or $K_i$ value of less than about 10 µM for the inhibition of a desired MP. Preferred compounds of the present invention have $K_i$'s or $IC_{50}$'s of ≦1 µM. More preferred compounds of the present invention have $K_i$'s or $IC_{50}$'s of ≦0.1 µM. Even more preferred compounds of the present invention have $K_i$'s or $IC_{50}$'s of ≦0.01 µM. Still more preferred compounds of the present invention have $K_i$'s or $IC_{50}$'s of ≦0.001 µM.

TNF PBMC Assay

Human peripheral blood mononuclear cells (PBMC) were obtained from normal donor blood by leukophoresis and isolated by Ficoll-Paque density separation. PBMCs were suspended in 0.5 mL RPMI 1640 with no serum at $2\times10^6$ cells/mL in 96 well polystyrene plates. Cells were preincubated 10 minutes with compound, then stimulated with 1 µg/mL LPS (Lipopolysaccharide, *Salmonella typhimurium*) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 mL. 225 µL of blood is plated directly into sterile polypropylene tubes. Compounds are diluted in DMSO/serum free media and added to the blood samples so the final concentration of compounds are 50, 10, 5, 1, 0.5, 0.1, and 0.01 µM. The final concentration of DMSO does not exceed 0.5%. Compounds are preincubated for 15 minutes before the addition of 100 µg/mL LPS. Plates are incubated for 5 hours in an atmosphere of 5% $CO_2$ in air. At the end of 5 hours, 750 µL of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the $IC_{50}$ value.

TNF Induction in Mice

Test compounds are administered to mice either I.P. or P.O. at time zero. Immediately following compound administration, mice receive an I.P. injection of 20 mg of D-galactosamine plus 10 µg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Assays

The enzymatic activities of recombinant MMP-1, 2, 3, 7, 8, 9, 10, 12, 13, 14, 15, and 16 were measured at 25° C. with a fluorometric assay (Copeland, R. A. et al. *Bioorganic Med. Chem. Lett.* 1995, 5, 1947–1952). Final enzyme concentrations in the assay were between 0.05 and 10 nM depending on the enzyme and the potency of the inhibitor tested. The permissive peptide substrate, MCA-Pro-Leu-Gly-Leu-DPA-Ala-Arg-$NH_2$, was present at a final concentration of 10 µM in all assays. Initial velocities, in the presence or absence of inhibitor, were measured as slopes of the linear portion of the product progress curves. $IC_{50}$ values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis*, Wiley-VHC, New York, 1996, pp 187–223). All of the compounds studied here were assumed to act as competitive inhibitors of the enzyme, binding to the active site Zn atom as previously demonstrated by crystallographic studies of MMP-3 complexed with related hydroxamic acids (Rockwell, A. et al. *J. Am. Chem. Soc.* 1996, 118, 10337–10338). Based on the assumption of competitive inhibition, the $IC_{50}$ values were converted to $K_i$ values as previously described.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM.

Using the methodology described above, a number of compounds of the present invention were found to exhibit $K_i$'s of $\leq 10$ μM, thereby confirming the utility of the compounds of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of an inflammatory disorder (as defined previously). In another embodiment, the package insert states that the pharmaceutical composition can be used in combination (as defined previously) with a second therapeutic agent to treat an inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is *Remington's Pharmaceutical Sciences*.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 mg to about 100 mg of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, a standard reference text in this field.

The compounds of the present invention may be administered in combination with a second therapeutic agent, especially non-steroidal anti-inflammatory drugs (NSAID's). The compound of the present invention and such second therapeutic agent can be administered separately or as a physical combination in a single dosage unit, in any dosage form and by various routes of administration, as described above.

The compound of the present invention may be formulated together with the second therapeutic agent in a single dosage unit (that is, combined together in one capsule, tablet, powder, or liquid, etc.). When the compound of the present invention and the second therapeutic agent are not formulated together in a single dosage unit, the compound of the present invention and the second therapeutic agent may be administered essentially at the same time, or in any order; for example the compound of the present invention may be administered first, followed by administration of the second agent. When not administered at the same time, preferably the administration of the compound of the present invention and the second therapeutic agent occurs less than about one hour apart, more preferably less than about 5 to 30 minutes apart.

Preferably the route of administration of the compound of the present invention is oral. Although it is preferable that the compound of the present invention and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of the present invention when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of the present invention. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:
1. A compound of Formula (I):

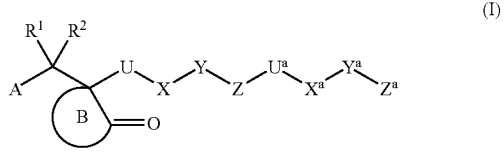

or a stereoisomer or pharmaceutically acceptable salt or solvate form thereof, wherein:
  A is —C(O)NHOH, —C(O)NHOR$^5$, —C(O)NHOR$^6$;
  ring B is substituted with 0–3 R$^3$ and is a 5–6 membered ring consisting of carbon atoms, 1 N, 0–1 additional carbonyl groups, and 0 double bond;
  U is absent;
  X is absent or is $C_{1-10}$ alkylene, $C_{2-10}$ alkenylene, or $C_{2-10}$ alkynylene;
  Y is absent;
  Z is a six-membered carbocycle substituted with 0–5 R$^b$;
  U$^a$ is O;
  X$^a$ is absent or is $C_{1-10}$ alkylene, $C_{2-10}$ alkenylene, or $C_{2-10}$ alkynylene;
  Y$^a$ is absent or is O, NR$^{a1}$, S(O)$_p$, or C(O);
  Z$^a$ is substituted with 0–5 R$^c$ and selected from pyridyl and quinolinyl;
  provided that U$^a$, and Y$^a$, are not together a O—O, O—S(O)$_p$ group;
  R$^1$ is Q, —C$_{1-6}$ alkylene-Q, —C$_{2-6}$ alkenylene-Q, —C$_{2-6}$ alkynylene-Q, —(CR$^a$R$^{a1}$)$_r$O(CR$^a$R$^{a1}$)$_s$-Q, —(CR$^a$R$^{a1}$)$_r$NR$^a$(CR$^a$R$^{a1}$)$_s$-Q, —(CR$^a$R$^{a1}$)$_r$C(O) (CR$^a$R$^{a1}$)$_s$-Q, —(CR$^a$R$^{a1}$)$_r$C(O)O(CR$^a$R$^{a1}$)$_s$-Q, —(CR$^a$R$^{a1}$)$_r$OC(O)(CR$^a$R$^{a1}$)$_s$-Q, —(CR$^a$R$^{a1}$)$_r$C(O) NR$^a$R$^{a1}$, —(CR$^a$R$^{a1}$)$_r$C(O)NR$^a$(CR$^a$R$^{a1}$)$_s$-Q, —(CR$^a$R$^{a1}$)$_r$NR$^a$C(O)(CR$^a$R$^{a1}$)$_s$-Q, —(CR$^a$R$^{a1}$)$_r$OC (O)O(CR$^a$R$^{a1}$)$_s$-Q, —(CR$^a$R$^{a1}$)$_r$OC(O)NR$^a$(CR$^a$R$^{a1}$)$_s$-Q, —(CR$^a$R$^{a1}$)$_r$NR$^a$C(O)O(CR$^a$R$^{a1}$)$_s$-Q, —(CR$^a$R$^{a1}$)$_r$NR$^a$C(O)NR$^a$(CR$^a$R$^{a1}$)$_s$-Q, —(CR$^a$R$^{a1}$)$_s$S(O)$_p$ (CR$^a$R$^{a1}$)$_s$-Q, —(CR$^a$R$^{a1}$)$_r$SO$_2$NR$^a$(CR$^a$R$^{a1}$)$_s$-Q, —(CR$^a$R$^{a1}$)$_r$NR$^a$SO$_2$(CR$^a$R$^{a1}$)$_s$-Q, or —(CR$^a$R$^{a1}$)$_r$ NR$^a$SO$_2$NR$^a$(CR$^a$R$^{a1}$)$_s$-Q;
  R$^2$ is Q$^1$, —C$_{1-6}$ alkylene-Q$^1$, —C$_{2-6}$ alkenylene-Q$^1$, —C$_{2-6}$ alkynylene-Q$^1$, —(CR$^a$R$^{a1}$)$_r$O(CR$^a$R$^{a1}$)$_s$-Q$^1$, —(CR$^a$R$^{a1}$)$_r$NR$^a$(CR$^a$R$^{a1}$)$_s$-Q$^1$, —(CR$^a$R$^{a1}$)$_r$C(O) (CR$^a$R$^{a1}$)$_s$-Q$^1$, —(CR$^a$R$^{a1}$)$_r$C(O)O(CR$^a$R$^{a1}$)$_s$-Q$^1$, —(CR$^a$R$^{a1}$)$_r$OC(O)(CR$^a$R$^{a1}$)$_s$-Q$^1$, —(CR$^a$R$^{a1}$)$_r$C(O) NR$^a$R$^{a1}$, —(CR$^a$R$^{a1}$)$_r$C(O)NR$^a$(CR$^a$R$^{a1}$)$_s$-Q$^1$, —(CR$^a$R$^{a1}$)$_r$NR$^a$C(O)(CR$^a$R$^{a1}$)$_s$-Q$^1$, —(CR$^a$R$^{a1}$)$_r$OC (O)O(CR$^a$R$^{a1}$)$_s$-Q$^1$, —(CR$^a$R$^{a1}$)$_r$OC(O)NR$^a$(CR$^a$R$^{a1}$)$_s$ -Q$^1$, —(CR$^a$R$^{a1}$)$_r$NR$^a$C(O)NR$^a$(CR$^a$R$^{a1}$)$_s$Q$^1$, —(CR$^a$R$^{a1}$$_2$)$_s$S(O)$_p$(CR$^a$R$^{a1}$)$_s$-Q$^1$, —(CR$^a$R$^{a1}$)$_r$ SO$_2$NR$^a$(CR$^a$R$^{a1}$)$_s$-Q$^1$, —(CR$^a$R$^{a1}$)$_r$NR$^a$SO$_2$ (CR$^a$R$^{a1}$)$_s$-Q$^1$, or —(CR$^a$R$^{a1}$)$_r$NR$^a$SO$_2$NR$^a$(CR$^a$R$^{a1}$)$_s$ -Q$^1$;
  R$^3$ is Q, —C$_{1-6}$ alkylene-Q, —C$_{2-6}$ alkenylene-Q, —C$_{2-6}$ alkynylene-Q, —(CR$^a$R$^{a1}$)$_r$O(CR$^a$R$^{a1}$)$_s$-Q, —(CR$^a$R$^{a1}$)$_r$NR$^a$(CR$^a$R$^{a1}$)$_s$-Q, —(CR$^a$R$^{a1}$)$_r$C(O) (CR$^a$R$^{a1}$)$_s$-Q, —(CR$^a$R$^{a1}$)$_r$C(O)O(CR$^a$R$^{a1}$)$_s$-Q, —(CR$^a$R$^{a1}$)$_r$OC(O)(CR$^a$R$^{a1}$)$_s$-Q, —(CR$^a$R$^{a1}$)$_r$C(O) NR$^a$R$^{a1}$, —(CR$^a$R$^{a1}$)$_r$C(O)NR$^a$(CR$^a$R$^{a1}$)$_s$-Q, —(CR$^a$R$^{a1}$)$_r$NR$^a$C(O)(CR$^a$R$^{a1}$)$_s$-Q, —(CR$^a$R$^{a1}$)$_r$OC (O)O(CR$^a$R$^{a1}$)$_s$-Q, —(CR$^a$R$^{a1}$)$_r$OC(O)NR$^a$(CR$^a$R$^{a1}$)$_s$-Q, —(CR$^a$R$^{a1}$)$_r$NR$^a$C(O)O(CR$^a$R$^{a1}$)$_s$-Q, —(CR$^a$R$^{a1}$)$_r$NR$^a$C(O)NR$^a$(CR$^a$R$^{a1}$)$_s$-Q, —(CR$^a$R$^{a1}$)$_r$S(O)$_p$ $(CR^aR^{a1})_s$-Q, —$(CR^aR^{a1})_r$SO$_2$NR$^a$(CR$^a$R$^{a1}$)$_s$-Q, —$(CR^aR^{a1})_r$NR$^a$SO$_2$(CR$^a$R$^{a1}$)$_s$-Q, or —$(CR^aR^{a1})_r$NR$^a$SO$_2$NR$^a$(CR$^a$R$^{a1}$)$_s$-Q;

each Q is, independently at each occurrence, H, CHF$_2$, CH$_2$F, CF$_3$, or C$_{3-13}$ carbocycle substituted with 0–5 R$^d$;

each Q$^1$ is, independently at each occurrence, H or a C$_{3-13}$ carbocycle substituted with 0–5 R$^d$;

each R$^a$ is, independently at each occurrence, H, C$_{1-6}$ alkyl, phenyl, or benzyl;

each R$^{a1}$ is, independently at each occurrence, H, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, or —(CH$_2$)$_r$-3–8 membered carbocyclic ring and substituted with 0–3 R$^{c1}$;

each R$^{a2}$ is, independently at each occurrence, C$_{1-4}$ alkyl, phenyl, or benzyl;

each R$^b$ is, independently at each occurrence, C$_{1-6}$ alkyl substituted with 0–1 R$^{c1}$, OR$^a$, SR$^a$, Cl, F, Br, I, =O, CN, NO$_2$, —NR$^a$R$^{a1}$, —C(O)R$^a$, —C(O)OR$^a$, —C(O)NR$^a$R$^{a1}$, —C(S)NR$^a$R$^{a1}$, —NR$^a$C(O)NR$^a$R$^{a1}$, —OC(O)NR$^a$R$^{a1}$, —NR$^a$C(O)OR$^a$, —S(O)$_2$NR$^a$R$^{a1}$, —NR$^a$S(O)$_2$R$^{a3}$, —NR$^a$S(O)$_2$NR$^a$R$^{a1}$, —OS(O)$_2$NR$^a$R$^{a1}$, —S(O)$_p$R$^{a3}$, CF$_3$, —CF$_2$CF$_3$, CHF$_2$, CH$_2$F, or phenyl;

each R$^{a3}$ is, independently at each occurrence, H, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, or —(CH$_2$)$_r$-3–8 membered carbocyclic ring and substituted with 0–3 R$^{c1}$;

each R$^c$ is, independently at each occurrence, H, OR$^a$, Cl, F, Br, I, =O, CN, NO$_2$, CF$_3$, —CF$_2$CF$_3$, CH$_2$F, CHF$_2$, —(CR$^a$R$^{a1}$)$_r$NR$^a$R$^{a1}$, —(CR$^a$R$^{a1}$)$_r$C(=NCN)NR$^a$R$^{a1}$, —(CR$^a$R$^{a1}$)$_r$C(=NR$^a$)NR$^a$R$^{a1}$, —(CR$^a$R$^{a1}$)$_r$C(=NOR$^a$)NR$^a$R$^{a1}$, —(CR$^a$R$^{a1}$)$_r$C(O)NR$^a$OH, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(S)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$C(S)NR$^a$R$^{a1}$, —(CR$^a$R$^{a1}$)$_r$OC(O)NR$^a$R$^{a1}$, —(CR$^a$R$^{a1}$)$_r$NR$^a$C(O)OR$^{a1}$, —(CR$^a$R$^{a1}$)$_r$NR$^a$C(O)NR$^a$R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, —(CR$^a$R$^{a1}$)$_r$NR$^a$SO$_2$NR$^a$R$^{a1}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, or —(CR$^a$R$^{a1}$)$_r$—C$_{3-10}$ carbocycle substituted with 0–2 R$^{c1}$;

each R$^{c1}$ is, independently at each occurrence, H, C$_{1-4}$ alkyl, OR$^a$, Cl, F, Br, I, =O, CF$_3$, —CN, NO$_2$, C(O)R$^a$, C(O)OR$^a$, C(O)NR$^a$R$^a$, or S(O)$_p$R$^a$;

each R$^d$ is, independently at each occurrence, C$_{1-6}$ alkyl, OR$^a$, Cl, F, Br, I, =O, CN, NO$_2$, —NR$^a$R$^{a1}$, —C(O)R$^a$, —C(O)OR$^a$, —C(O)NR$^a$R$^{a1}$, —C(S)NR$^a$R$^{a1}$, —NR$^a$C(O)NR$^a$R$^{a1}$, —OC(O)NR$^a$R$^{a1}$, —NR$^a$C(O)O, —S(O)$_2$NR$^a$R$^{a1}$, —NR$^a$S(O)$_2$R$^{a3}$, —NR$^a$S(O)$_2$NR$^a$R$^{a1}$, —OS(O)$_2$NR$^a$R$^{a1}$, —S(O)$_p$R$^{a3}$, CF$_3$, CF$_2$CF$_3$, or C$_{3-10}$ carbocycle;

each R$^5$ is, independently at each occurrence, C$_{1-10}$ alkyl substituted with 0–2 R$^b$, or C$_{1-8}$ alkyl substituted with 0–2 R$^e$;

each R$^e$ is, independently at each occurrence, phenyl substituted with 0–2 R$^b$ or biphenyl substituted with 0–2 R$^b$;

each R$^6$ is, independently at each occurrence, phenyl, naphthyl, C$_{1-10}$ alkyl-phenyl-C$_{1-6}$ alkyl-, C$_{3-11}$ cycloalkyl, C$_{1-6}$ alkylcarbonyloxy-C$_{1-3}$ alkyl-, C$_{1-6}$ alkoxycarbonyloxy-C$_{1-3}$ alkyl-, C$_{2-10}$ alkoxycarbonyl, C$_{3-6}$ cycloalkylcarbonyloxy-C$_{1-3}$ alkyl-, C$_{3-6}$ cycloalkoxycarbonyloxy-C$_{1-3}$ alkyl-, C$_{3-6}$ cycloalkoxycarbonyl, phenoxycarbonyl, phenyloxycarbonyloxy-C$_{1-3}$ alkyl-, phenylcarbonyloxy-C$_{1-3}$ alkyl-, C$_{1-6}$ alkoxy-C$_{1-6}$ alkylcarbonyloxy-C$_{1-3}$ alkyl-, [5-(C$_1$–C$_5$ alkyl)-1,3-dioxa-cyclopenten-2-one-yl]methyl, [5-(R$^a$)-1,3-dioxa-cyclopenten-2-one-yl]methyl, (5-aryl-1,3-dioxa-cyclopenten-2-one-yl)methyl, —C$_{1-10}$ alkyl-NR$^7$R$^{7a}$, —CH(R$^8$)OC(=O)R$^9$, or —CH(R$^8$)OC(=O)OR$^9$;

R$^7$ is H, C$_{1-10}$ alkyl, C$_{2-6}$ alkenyl, C$_{3-6}$ cycloalkyl-C$_{1-3}$ alkyl-, or phenyl-C$_{1-6}$ alkyl-;

R$^{7a}$ is H, C$_{1-10}$ alkyl, C$_{2-6}$ alkenyl, C$_{3-6}$ cycloalkyl-C$_{1-3}$ alkyl-, or phenyl-C$_{1-6}$ alkyl-;

each R$^8$ is, independently at each occurrence, H or C$_{1-4}$ linear alkyl;

each R$^9$ is, independently at each occurrence, H, C$_{1-8}$ alkyl substituted with 1–2 R$^f$, C$_{3-8}$ cycloalkyl substituted with 1–2 R$^f$, or phenyl substituted with 0–2 R$^b$;

each R$^f$ is, independently at each occurrence, C$_{1-4}$ alkyl, C$_{3-8}$ cycloalkyl, C$_{1-5}$ alkoxy, or phenyl substituted with 0–2 R$^b$;

m, at each occurrence, is selected from 0, 1, 2 and 3;

p, at each occurrence, is selected from 0, 1, and 2;

r, at each occurrence, is selected from 0, 1, 2, 3, and 4;

s, at each occurrence, is selected from 0, 1, 2, 3, and 4; and t, at each occurrence, is selected from 1, 2, 3, and 4.

2. A compound according to claim 1, wherein:

X is absent or is C$_{1-3}$ alkylene;

X$^a$ is absent or is C$_{1-4}$ alkylene, C$_{2-4}$ alkenylene, or C$_{2-4}$ alkynylene;

Y$^a$ is absent or is O or NR$^{a1}$;

R$^1$ is Q, —C$_{1-6}$ alkylene-Q, —C$_{2-6}$ alkenylene-Q, —C$_{2-6}$ alkynylene-Q, —(CR$^a$R$^{a1}$)$_r$O(CR$^a$R$^{a1}$)$_s$-Q, —(CR$^a$R$^{a1}$)$_r$NR$^a$(CR$^a$R$^{a1}$)$_s$-Q, —(CR$^a$R$^{a1}$)$_r$C(O)(CR$^a$R$^{a1}$)$_s$-Q, —(CR$^a$R$^{a1}$)$_r$C(O)O(CR$^a$R$^{a1}$)$_s$-Q, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$-Q, —(CR$^a$R$^{a1}$)$_r$S(O)$_p$(CR$^a$R$^{a1}$)$_s$-Q, —(CR$^a$R$^{a1}$)$_r$SO$_2$NR$^a$(CR$^a$R$^{a1}$)$_s$-Q, or —(CR$^a$R$^{a1}$)$_r$NR$^a$SO$_2$(CR$^a$R$^{a1}$)$_s$-Q;

R$^2$ is Q$^1$, C$_{1-6}$ alkylene-Q$^1$, C$_{2-6}$ alkenylene-Q$^1$, C$_{2-6}$ alkynylene-Q$^1$, —(CR$^a$R$^{a1}$)$_r$O(CR$^a$R$^{a1}$)$_s$-Q$^1$, —(CR$^a$R$^{a1}$)$_r$NR$^a$(CR$^a$R$^{a1}$)$_s$-Q$^1$, —(CR$^a$R$^{a1}$)$_r$C(O)(CR$^a$R$^{a1}$)$_s$-Q$^1$, —(CR$^a$R$^{a1}$)$_r$C(O)O(CR$^a$R$^{a1}$)$_s$-Q$^1$, —(CR$^a$R$^{a1}$)$_r$OC(O)(CR$^a$R$^{a1}$)$_s$-Q$^1$, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$-Q$^1$, —(CR$^a$R$^{a1}$)$_r$NR$^a$C(O)(CR$^a$R$^{a1}$)$_s$-Q$^1$, —(CR$^a$R$^{a1}$)$_2$)$_r$S(O)$_p$(CR$^a$R$^{a1}$)$_s$-Q$^1$, —(CR$^a$R$^{a1}$)$_r$SO$_2$NR$^a$(CR$^a$R$^{a1}$)$_s$-Q$^1$, or —(CR$^a$R$^{a1}$)$_r$NR$^a$SO$_2$(CR$^a$R$^{a1}$)$_s$-Q$^1$;

R$^3$ is Q, —C$_{1-6}$ alkylene-Q, —C$_{2-6}$ alkenylene-Q, —C$_{2-6}$ alkynylene-Q, —(CR$^a$R$^{a1}$)$_r$O(CR$^a$R$^{a1}$)$_s$-Q, —(CR$^a$R$^{a1}$)$_r$NR$^a$(CR$^a$R$^{a1}$)$_s$-Q, —(CR$^a$R$^{a1}$)$_r$C(O)(CR$^a$R$^{a1}$)$_s$-Q, —(CR$^a$R$^{a1}$)$_r$C(O)O(CR$^a$R$^{a1}$)$_s$-Q, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$-Q, —(CR$^a$R$^{a1}$)$_r$NR$^a$C(O)(CR$^a$R$^{a1}$)$_s$-Q, —(CR$^a$R$^{a1}$)$_r$S(O)$_p$(CR$^a$R$^{a1}$)$_s$-Q, —(CR$^a$R$^{a1}$)$_r$SO$_2$NR$^a$(CR$^a$R$^{a1}$)$_s$-Q, or —(CR$^a$R$^{a1}$)$_r$NR$^a$SO$_2$(CR$^a$R$^{a1}$)$_s$-Q;

each Q is, independently at each occurrence, H, CHF$_2$, CH$_2$F, CF$_3$, or a C$_{3-13}$ carbocycle substituted with 0–3 R$^d$;

each R$^a$ is, independently at each occurrence, H, C$_{1-6}$ alkyl, phenyl, or benzyl;

each R$^{a1}$ is, independently at each occurrence, H, C$_{1-6}$ alkyl, C$_{2-6}$ alkenyl, C$_{2-6}$ alkynyl, or —(CH$_2$)$_r$-3–8 membered carbocyclic ring;

each R$^c$ is, independently at each occurrence, H, OR$^a$, Cl, F, Br, =O, CN, NO$_2$, CF$_3$, CH$_2$F, CHF$_2$, —CF$_2$CF$_3$, —(CR$^a$R$^{a1}$)$_r$NR$^a$R$^{a1}$, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, or —(CH$_2$)$_r$—C$_{3-6}$ carbocycle substituted with 0–2 R$^{c1}$;

each R$^d$ is, independently at each occurrence, C$_{1-6}$ alkyl, OR$^a$, Cl, F, Br, =O, —CN, NO$_2$, —NR$^a$R$^{a1}$, —C(O)R$^a$, —C(O)OR$^a$, —C(O)NR$^a$R$^{a1}$, —S(O)$_2$NR$^a$R$^{a1}$, —NR$^a$S(O)$_2$NR$^a$R$^{a1}$, —S(O)$_p$R$^{a3}$, CF$_3$, or C$_{3-6}$ carbocycle;

each R$^5$ is, independently at each occurrence, C$_{1-6}$ alkyl substituted with 0–2 R$^b$, and C$_{1-4}$ alkyl substituted with 0–2 R$^e$;

each R$^9$ is, independently at each occurrence, H, C$_{1-6}$ alkyl substituted with 1–2 R$^f$, C$_{3-6}$ cycloalkyl substituted with 1–2 R$^f$, or phenyl substituted with 0–2 R$^b$; and each R$^f$ is, independently at each occurrence, C$_{1-4}$ alkyl, C$_{3-6}$ cycloalkyl, C$_{1-5}$ alkoxy, or phenyl substituted with 0–2 R$^b$.

3. A compound according to claim 2, wherein:
A is —C(O)NHOH;
X is absent or is methylene or ethylene;
R$^1$ is Q, —C$_{1-6}$ alkylene-Q, —C$_{2-6}$ alkenylene-Q, —C$_{2-6}$ alkynylene-Q, —(CH$_2$)$_r$O(CH$_2$)$_s$-Q, —(CH$_2$)$_r$NR$^a$(CH$_2$)$_s$-Q, —(CH$_2$)$_r$C(O)(CH$_2$)$_s$-Q, —(CH$_2$)$_r$C(O)O(CH$_2$)$_s$-Q, —(CH$_2$)$_r$C(O)NR$^a$R$^{a1}$, —(CH$_2$)$_r$C(O)NR$^a$(CH$_2$)$_s$-Q, —(CH$_2$)$_r$NR$^a$C(O)(CH$_2$)$_s$-Q, —(CH$_2$)$_r$S(O)$_p$(CH$_2$)$_s$-Q, —(CH$_2$)$_r$SO$_2$NR$^a$(CH$_2$)$_s$-Q, or —(CH$_2$)$_r$NR$^a$SO$_2$(CH$_2$)$_s$-Q;

R$^2$ is Q$^1$, —C$_{1-6}$ alkylene-Q$^1$, —C$_{2-6}$ alkenylene-Q$^1$, —C$_{2-6}$ alkynylene-Q$^1$, —(CR$^a$R$^{a1}$)$_r$O(CR$^a$R$^{a1}$)$_s$-Q$^1$, —(CR$^a$R$^{a1}$)$_r$NR$^a$(CR$^a$R$^{a1}$)$_s$-Q$^1$, —(CR$^a$R$^{a1}$)$_r$C(O)(CR$^a$R$^{a1}$)$_s$-Q$^1$, —(CR$^a$R$^{a1}$)$_r$C(O)O(CR$^a$R$^{a1}$)$_s$-Q$^1$, —(CR$^a$R$^{a1}$)$_r$C(O)NR$^a$(CR$^a$R$^{a1}$)$_s$-Q$^1$, —(CR$^a$R$^{a1}$)$_r$NR$^a$C(O)(CR$^a$R$^{a1}$)$_s$-Q$^1$, —(CR$^a$R$^{a1}$)$_r$S(O)$_p$(CR$^a$R$^{a1}$)$_s$-Q$^1$, —(CR$^a$R$^{a1}$)$_r$SO$_2$NR$^a$(CR$^a$R$^{a1}$)$_s$-Q$^1$, or —(CR$^a$R$^{a1}$)$_r$NR$^a$SO$_2$(CR$^a$R$^{a1}$)$_s$-Q$^1$;

R$^3$ is Q, —C$_{1-6}$ alkylene-Q, —C$_{2-6}$ alkenylene-Q, —C$_{2-6}$ alkynylene-Q, —(CH$_2$)$_r$O(CH$_2$)$_s$-Q, —(CH$_2$)$_r$NR$^a$(CH$_2$)$_s$-Q, —(CH$_2$)$_r$C(O)(CH$_2$)$_s$-Q, —(CH$_2$)$_r$C(O)O(CH$_2$)$_s$-Q, —(CH$_2$)$_r$C(O)NR$^a$R$^{a1}$, —(CH$_2$)$_r$C(O)NR$^a$(CH$_2$)$_s$-Q, —(CH$_2$)$_r$NR$^a$C(O)(CH$_2$)$_s$-Q, —(CH$_2$)$_r$S(O)$_p$(CH$_2$)$_s$-Q, —(CH$_2$)$_r$SO$_2$NR$^a$(CH$_2$)$_s$-Q, or —(CH$_2$)$_r$NR$^a$SO$_2$(CH$_2$)$_s$-Q;

each Q is, independently at each occurrence, H or a C$_{3-8}$ carbocycle substituted with 0–3 R$^d$;

each R$^{a3}$ is, independently at each occurrence, H, C$_{1-6}$ alkyl, C$_{2-6}$ alkenyl, or —(CH$_2$)$_r$-3–8 membered carbocyclic ring and substituted with 0–3 R$^{c1}$;

each R$^c$ is, independently at each occurrence, H, OR$^a$, Cl, F, Br, =O, CF$_3$, CH$_2$F, CHF$_2$, —(CR$^a$R$^{a1}$)$_r$NR$^a$R$^{a1}$, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^a$)$_r$NR$^a$SO$_2$R$^{a3}$, C$_{1-6}$ alkyl, C$_{2-6}$ alkenyl, C$_{2-6}$ alkynyl, C$_{3-6}$ cycloalkyl substituted with 0–1 R$^{c1}$, or phenyl substituted with 0–2 R$^{c1}$;

each R$^d$ is, independently at each occurrence, C$_{1-6}$ alkyl, OR$^a$, Cl, F, Br, =O, NR$^a$R$^{a1}$, C(O)R$^a$, C(O)OR$^a$, C(O)NR$^a$R$^{a1}$, S(O)$_2$NR$^a$R$^{a1}$, NR$^a$S(O)$_2$R$^{a3}$, S(O)$_p$R$^{a3}$, CF$_3$ or phenyl;

r, at each occurrence, is selected from 0, 1, 2, and 3;
s, at each occurrence, is selected from 0, 1, 2, and 3; and
t, at each occurrence, is selected from 0, 1, 2, and 3.

4. A compound according to claim 3, wherein the compound is of Formula (II):

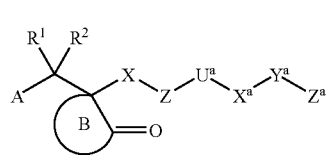

(II)

or a stereoisomer or pharmaceutically acceptable or solvate salt form thereof, wherein;

A is —C(O)NHOH;
X is absent, or is methylene;
ring B is substituted with 0–2 R$^3$ and is a 5–6 membered ring consisting of carbon atoms, 1 N, 0–1 additional carbonyl groups, and 0 double bond;
Z is phenyl substituted with 0–4 R$^b$;
Z$^a$ is substituted with 0–3 R$^c$ and selected from pyridyl and quinolinyl;
each Q is, independently at each occurrence, H or a C$_{3-10}$ carbocycle substituted with 0–5 R$^d$;
each R$^{a1}$ is, independently at each occurrence, H, C$_{1-6}$ alkyl, phenyl, or benzyl;
each R$^{a3}$ is, independently at each occurrence, H, C$_{1-6}$ alkyl, phenyl, or benzyl; and
each R$^c$ is, independently at each occurrence, H, OR$^a$, Cl, F, Br, =O, CF$_3$, CH$_2$F, CHF$_2$, —(CR$^a$R$^{a1}$)$_r$NR$^a$R$^{a1}$, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl, C$_{2-6}$ alkenyl, C$_{2-6}$ alkynyl, or phenyl substituted with 0–2 R$^{c1}$.

5. A compound according to claim 4, wherein:
Y$^a$ is absent or is O;
R$^2$ is Q$^1$, —C$_{1-6}$ alkylene-Q$^1$, —C$_{2-6}$ alkenylene-Q$^1$, —C$_{2-6}$ alkynylene-Q$^1$, —(CH$_2$)$_r$O(CH$_2$)$_s$-Q$^1$, —(CH$_2$)$_r$NR$^a$(CH$_2$)$_s$-Q$^1$, —(CH$_2$)$_r$C(O)(CH$_2$)$_s$-Q$^1$, —(CH$_2$)$_r$C(O)O(CH$_2$)$_s$-Q$^1$, —(CH$_2$)$_r$C(O)NR$^a$(CH$_2$)$_s$-Q$^1$, —(CH$_2$)$_r$NR$^a$C(O)(CH$_2$)$_s$-Q$^1$, —(CH$_2$)$_r$S(O)$_p$(CH$_2$)$_s$-Q$^1$, —(CH$_2$)$_r$SO$_2$NR$^a$(CH$_2$)$_s$-Q$^1$, or —(CH$_2$)$_r$NR$^a$SO$_2$(CH$_2$)$_s$-Q$^1$;

R$^3$ is H, C$_{1-4}$ alkyl, C$_{2-4}$ alkenyl, C$_{2-4}$ alkynyl, phenyl, or benzyl;

each Q is, independently at each occurrence, H or a C$_{3-6}$ carbocycle;

each R$^a$ is, independently at each occurrence, H or C$_{1-4}$ alkyl;

each R$^{a1}$ is, independently at each occurrence, H or C$_{1-4}$ alkyl;

each R$^{a3}$ is, independently at each occurrence, H, C$_{1-4}$ alkyl, phenyl, or benzyl; and each R$^c$ is, independently at each occurrence, C$_{1-6}$ alkyl, C$_{2-6}$ alkenyl, C$_{2-6}$ alkynyl, OR$^a$, Cl, F, Br, =O, CF$_3$, CH$_2$F, CHF$_2$, —NR$^a$R$^{a1}$, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, or phenyl.

6. A compound according to claim 5, wherein the compound is of Formula (III):

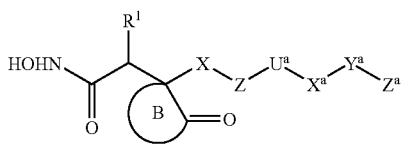

(III)

or a stereoisomer or pharmaceutically acceptable salt or solvate form thereof, wherein;

X is absent, or is methylene;

$R^1$ is H or $C_{1-6}$ alkylene;

each $Q^1$ is, independently at each occurrence, H, $C_{3-6}$ cycloalkyl substituted with 0–1 $R^d$, or phenyl substituted with 0–2 $R^d$;

m, at each occurrence, is selected from 0, 1, and 2;

r, at each occurrence, is selected from 0, 1, and 2; and s, at each occurrence, is selected from 0, 1, and 2.

7. A compound according to claim 6, wherein:

Z is phenyl substituted with 0–1 $R^b$;

each $R^b$ is, independently at each occurrence, $C_{1-6}$ alkyl, $OR^a$, Cl, F, Br, $-NR^aR^{a1}$, $-C(O)R^a$, $-C(O)OR^a$, $-C(O)NR^aR^{a1}$, $-S(O)_2NR^aR^{a1}$, $-NR^aS(O)_2R^{a3}$, $-S(O)_pR^{a3}$, or $CF_3$;

each $R^c$ is, independently at each occurrence, $C_{1-6}$ alkyl, $C_{2-6}$ alkenyl, $C_{2-6}$ alkynyl, $OR^a$, Cl, F, Br, =O, $-NR^aR^{a1}$, $CF_3$, $-(CR^aR^{a1})_rC(O)R^{a1}$, $-(CR^aR^{a1})_rC(O)OR^{a1}$, $-(CR^aR^{a1})_rC(O)NR^aR^1$, $-(CR^aR^{a1})_rN-R^aC(O)R^{a1}$, $-(CR^aR^{a1})_rS(O)_pR^{a3}$, $-(CR^aR^{a1})_rSO_2NR^aR^{a1}$, or $(CR^aR^{a1})_rNR^aSO_2R^{a3}$.

8. A compound of claim 1 selected from:

N-hydroxy-2-(1-methyl-3-{4-[(2-methyl-4-quinolinyl)methoxy]benzyl}2-oxo-3-piperidinyl)acetamide;

N-hydroxy-2-(1-methyl-3-{4-[(2-methyl-4-quinolinyl)methoxy]benzyl}-2-oxo-3-pyrrolidinyl)acetamide;

N-hydroxy-2-(1-methyl-3-{4-[(2-methyl-4-quinolinyl)methoxy]phenyl}-2-oxo-3-pyrrolidinyl)acetamide;

N-hydroxy-2-(1-(2-hydroxyethyl)-3-{4-[(2-methyl-4-quinolinyl)methoxy]phenyl}-2-oxo-3-pyrrolidinyl)acetamide; and or a stereoisomer or a pharmaceutically acceptable salt or solvate form thereof.

9. A pharmaceutical composition, comprising: a pharmaceutically acceptable carrier and a therapeutically effective amount of a compound of claim 1 or a pharmaceutically acceptable salt or solvate form thereof.

10. A pharmaceutical composition, comprising: a pharmaceutically acceptable carrier and a compound of claim 2 or a pharmaceutically acceptable salt or solvate form thereof.

11. A pharmaceutical composition, comprising: a pharmaceutically acceptable carrier and a compound of claim 3 or a pharmaceutically acceptable salt or solvate form thereof.

12. A pharmaceutical composition, comprising: a pharmaceutically acceptable carrier and a compound of claim 4 or a pharmaceutically acceptable salt or solvate form thereof.

13. A pharmaceutical composition, comprising: a pharmaceutically acceptable carrier and a compound of claim 5 or a pharmaceutically acceptable salt or solvate form thereof.

14. A pharmaceutical composition, comprising: a pharmaceutically acceptable carrier and a compound of claim 6 or a pharmaceutically acceptable salt or solvate form thereof.

15. A pharmaceutical composition, comprising: a pharmaceutically acceptable carrier and a compound of claim 7 or a pharmaceutically acceptable salt or solvate form thereof.

16. A pharmaceutical composition, comprising: a pharmaceutically acceptable carrier and a compound of claim 8 or a pharmaceutically acceptable salt or solvate form thereof.

\* \* \* \* \*